(12) United States Patent
Pelletier et al.

(10) Patent No.: US 8,008,346 B2
(45) Date of Patent: Aug. 30, 2011

(54) CHEMOTHERAPEUTIC AGENTS FOR INHIBITION OF PROTEIN TRANSLATION

(75) Inventors: Jerry Pelletier, Baie d'Urfé (CA); Marie-Ève Bordeleau, Montréal (CA); Lisa Lindqvist, Montréal (CA); Robert Francis, Laval (CA); Junichi Tanaka, Okinawa (JP)

(73) Assignee: The Royal University for the Advancement of Learning/McGill University, Montreal (CA)

( * ) Notice: Subject to any disclaimer, the term of this patent is extended or adjusted under 35 U.S.C. 154(b) by 198 days.

(21) Appl. No.: 11/996,341

(22) PCT Filed: Jul. 24, 2006

(86) PCT No.: PCT/CA2006/001217
§ 371 (c)(1),
(2), (4) Date: Jun. 23, 2008

(87) PCT Pub. No.: WO2007/009264
PCT Pub. Date: Jan. 25, 2007

(65) Prior Publication Data
US 2009/0118362 A1   May 7, 2009

(51) Int. Cl.
*A61K 31/335* (2006.01)
*C12N 5/00* (2006.01)
*C12N 5/02* (2006.01)

(52) U.S. Cl. ......................... 514/462; 435/375
(58) Field of Classification Search .................. 514/462; 435/375
See application file for complete search history.

(56) References Cited

OTHER PUBLICATIONS

Kassam (Expert Opinion on Emerging Drugs (2008) 13:323-343).*
Gonzalez (Tetrahedron (2001) 57:3487-3497).*
Gura et. al. (Science, 1997, 278:1041-1042).*
Johnson et. al. (British Journal of Cancer, 2001, 84:1424-1431).*
Shen, Y.-C., et al., Bioactive steroids from the Formosan Gorgonian Isis Hippuris, Chinese Pharm. J. 2000, 341-351, 52.
Bordeleau, M.E., et al., Functional characterization of IRESes by an inhibitor of the RNA helicase eIF4A, Nat. Chem. Biol. 2006, 213-220, 2.
Chao, C.-H., et al., Polyoxygenated steroids from the gorgonian Isis hippuris, J. Nat. Prod., 2005, 880-885, 68.
Higa, T. et al., Hippuristanols, cytotoxic polyoxygenated steroids from the gorgonian Isis hippuris. Chem Lett., 1981, 1647-1650, 11.
Adwankar, M., et al., Combination chemotherapy of early and advanced murine P388 leukaemia with bouvardin, cis-diamminedichloroplatinum and vincristine. Oncology, 1984, 370-373, 41.
Ahuja, D., et al., Inhibition of protein synthesis by didemnins: cell potency and SAR, J. Med. Chem. 2000, 4212-4218, 43.
Ahuja, D., et al., Inhibition of protein synthesis by didemnin B: how EF-I alpha mediates inhibition of translocation. Biochemistry, 2000, 4339-4346, 39.
Andrus, L., et al., Antiretroviral effects of deoxyhypusyl hydroxylase inhibitors: a hypusine-dependent host cell mechanism for replication of human immunodeficiency virus type 1 (HIV-I). Biochem. Pharmacol., 1998, 1807-1818, 55.
Antony, M., et al., Inhibition of mouse skin tumor promotion by tenuazonic acid. Cancer Lett, 1991 21-25, 61.
Benz, J., et al., Crystal structure of the ATPase domain of translation initiation factor 4A from *Saccharomyces cerevisiae*—the prototype of the Dead box protein family. Structure Fold. Des. 1999, 671-679, 7.
Bernstein, H. D., et al., Poliovirus mutant that does not selectively inhibit host cell protein synthesis. Mol Cell Biol 1985, 2913-2923, 5.
Caruthers, J. M., et al. Crystal structure of yeast initiation factor 4A, a Dead-box RNA helicase. Proc Natl Acad Sci U S A, 2000, 13080-13085, 97.
Chan, C. C, et al., eIF4A3 is a novel component of the exon junction complex. RNA, 2004, 200-209, 10.
Conroy, S. C, et al., Characterization of the 46,000-dalton subunit of eIF-4F. Arch Biochem Biophys, 1990, 363-371, 282.
Dong, Z., et al., Role of eIF3 p170 in controlling synthesis of ribonucleotide reductase M2 and cell growth. Oncogene, 2004, 3790-3801, 21.
Ferraiuolo, M. A. et al., A nuclear translation-like factor eIF4AIII is recruited to the mRNA during splicing and functions in nonsense-mediated decay. Proc Natl Acad Sci U S A, 2004, 4118-4123, 101.
Gonzalez, N., et al., New cytotoxic steroids from the gorgonian Isis hippuris. Structure-activity studies. Tetrahedron 2001, 3487-3497, 57.
Grifo, J.A., et al., RNA-stimulated ATPase activity of eukaryotic initiation factors. J Biol Chem, 1984, 8648-8654, 259.
Grollman, A.P. Inhibitors of protein biosynthesis. II. Mode of action of anisomycin. J. Biol. Chem. 1967, 3226-3233, 242.
Hanauske-Abel, H.M., et al., Inhibition of the GI-S transition of the cell cycle by inhibitors of deoxyhypusine hydroxylation. Biochim Biophys Acta 1994, 115-24, 1221.
Hershey, J. W. B., and Merrick, W. C., Initiation of Protein Synthesis. Cold Spring Habor Laboratory Press, 2000, Cold Spring Harbor.
Hershey, J. W. B., and Miyamoto, S., Translational control and Cancer. Cold Spring Habor Laboratory Press, 2000, Cold Spring Harbor.
Heys, S.D., et al. Measurement of tumour protein synthesis in vivo in human colorectal and breast cancer and its variability in separate biopsies from the same tumour. Clin Sci (Lond), 1991, 587-593, 80.
Higa, T., and Tanaka, J., Hippuristanols, cytotoxic polyoxygenated steroids from the Gorgonian Isis Hipuris, Chemistry Letters, 1981, 1647-1650.
Higa, T., et al., 18-oxygenated polyfunctional steriods from the gorgonian Isis hippuris. Tetrahed. Lett., 1981, 2777-2780, 22.
Hofs, H.P., et al., Potentiation of cisplatin antitumour activity by Ethyldeshydroxy-Sparsomycin in L1210 leukemia. Anticancer Res, 1992, 167-170, 12.

(Continued)

*Primary Examiner* — Marcos L Sznaidman

(57) ABSTRACT

The present invention relates to a anti-proliferative target for designing chemotherapeutic agents, which comprises a EIF4A protein having an amino acid sequence, as defined in claim 1.

16 Claims, 24 Drawing Sheets

OTHER PUBLICATIONS

Hofs, H.P., et al., Antitumour activity and retinotoxicity of ethyldeshydroxy-sparsomycin in mice. Eur J Cancer, 1995, 1526-1530, 9.

Johnson, E.R. and McKay, D.B., Crystallographic structure of the amino terminal domain of yeast initiation factor 4A, a representative Dead-box RNA helicase. RNA 1999, 1526-1534, 5.

Kaczka, E. A., et al., Discovery of inhibitory activity of tenuazonic acid for growth of human adenocarcinoma-1. Biochem Biophys Res Commun. 1964, 54-57, 14.

Kantarjian, H. M., et al., Homoharringtonine: history, current research, and future direction. Cancer, 2001, 1591-605, 92.

Lorsch, J. R., and Herschlag, D., The Dead box protein eIF4A. A cycle of nucleotide and RNA-dependent conformational changes. Biochemistry, 1998, 2194-2206, 37.

Lorsch, J. R., and Herschlag, D., The Dead box protein eIF4A. A minimal kinetic and thermodynamic framework reveals coupled binding of RNA and nucleotide. Biochemistry, 1998 2180-2193, 37.

Muller, H.J., and Boos, J., Use of L-asparaginase in childhood ALL., Crit Rev Oncol Hematol, 1998, 97-113, 28.

Neshat, M.S., et al., Enhanced sensitivity of PTEN-deficient tumors to inhibition of FRAP/mTOR. Proc Natl Acad Sci U S A, 2001, 10314-10319, 98.

Novac, O., et al., Inhibitors of protein synthesis identified by a high throughput multiplexed translation screen. Nucleic Acids Res, 2004, 902-915, 32.

Ottenheijm, H.C, and Van Den Broeck, L.A., The development of sparsomycin as an anti-tumour drug. Anticancer Drug Des, 1998, 333-337, 2.

Palacios, I.M., et al., An eIF4AIII-containing complex required for mRNA localization and nonsense-mediated mRNA decay. Nature, 2004, 427:753-757.

Pause, A., et al., Insulin-dependent stimulation of protein synthesis by phosphorylation of a regulator of 5'-cap function. Nature, 1994, 371:762-767.

Yoder-Hill, J., et al., The p46 subunit of eukaryotic initiation factor (eIF)-4F exchanges with eIF-4A. J Biol Chem 1993, 5566-5573, 268.

Zalacain, M., et al., The mode of action of the antitumor drug bouvardin, an inhibitor of protein synthesis in eukaryotic cells. FEBS Lett 1982, 95-97, 148.

Zalatnai, A., and Bocsi, J. Mimosine, a plant-derived amino acid induces apoptosis in human pancreatic cancer xenografts. Anticancer Res, 2003, 4007-4009, 23.

Chitnis, M.R. et al. Inhibition of macromolecular synthesis in P388 mouse leukemia ascites cells by bouvardin (NSC 259968). Tumori 1985, 71:261-6.

Shibuya, T.T.O. Tet al. eIF4AIII binds spliced mRNA in the exon junction complex and is essential for nonsense-mediated decay. Nat Struct Mol Biol 2004, 11:346-51.

Sonenberg, N. ATP/Mg++-dependent cross-linking of cap binding proteins to the 5' end of eukaryotic mRNA. Nucleic Acids Res. 1981, 9: 1643-56.

Pause, A., et al., Dominant negative mutants of mammalian translation initiation factor eIF-4A define a critical role for eIF-4F in cap-dependent and cap-independent initiation of translation. Embo J., 1994 1205-1215, 13.

Pause. A., and Sonenberg. N. Mutational analysis of a Dead box RNA helicase: the mammalian translation initiation factor eIF-4A. Embo J., 1992, 2643-2654, 11.

Pisarev, A.V., et al., Functional and structural similarities between the internal ribosome entry sites of hepatitis C virus and porcine teschovirus, a picornavirus. J Virol, 2004 4487-4497, 78.

Podsypanina, K., et al., An inhibitor of mTOR reduces neoplasia and normalizes p70/S6 kinase activity in Pten+/− mice. Proc Natl Acad Sci U S A. 2001, 10320-10325, 98.

Poulin, F., et al.. 4E-BP3, a new member of the eukaryotic initiation factor 4E-binding protein family. J Biol Chem, 1998, 14002-14007, 273.

Rao, C. B., et al., Metabolites of the gorgonian Isis hippuris from India. J. Nat. Products. 1988, 51:954-958.

Ray, B.K., et al., ATP-dependent unwinding of messenger RNA structure by eukaryotic initiation factors. J Biol Chem, 1985, 7651-7658, 260.

Richter-Cook, N.J., et al., Purification and characterization of a new eukaryotic protein translation factor. Eukaryotic initiation factor 4H. J Biol Chem 1998, 273:7579-87.

Rogers, G.W. Jr. et al., Biochemical and kinetic characterization of the RNA helicase activity of eukaryotic initiation factor 4A. J Biol Chem 1999, 274: 12236-44.

Shen, Y.-C, et al., Two new polyhydroxysteroids from the gorgonian Isis hippuris. Steroids 2001, 66:721-725.

Sheu, J.-H., et al., Hippuristerone A, a novel poly oxygenated steroid from the gorgonian Isis hippuris. Tetrahed. Lett. 2000, 41:7885-7888.

Svitkin. Y.V., et al., The requirement for eukaryotic initiation factor 4A (eIF4A) in translation is in direct proportion to the degree of mRNA 5' secondary structure. Rna 2001, 7:382-94.

Tanaka, J., . et al., New polyoxygenated steroids exhibiting reversal of multidrug resistance from the gorgonian Isis hippuris. Tetrahedron., 2002. 6259-6266, 58.

Uchida, N., A novel role of the mammalian GSPT/eRF3 associating with poly(A)-binding protein in Cap/Poly(A)-dependent translation. J Biol Chem, 2002, 50286-92, 277.

Van Den Broek, L.A., et al., Lipophilic analogues of sparsomycin as strong inhibitors of protein synthesis and tumor growth: a structure-activity relationship study. J Med Chem, 1989, 2002-2015, 32.

Vera, M. D., and Joullie. M.M. Natural products as probes of cell biology: 20 years of didemnin research. Med Res Rev, 2002, 102-145, 22.

Wilson, J.E., et al., Initiation of protein synthesis from the A site of the ribosome. Cell, 2000, 511-520, 102.

Wilson, J.E., et al., Naturally occurring dicistronic cricket paralysis virus RNA is regulated by two internal ribosome entry sites. Mol Cell Biol, 2000, 4990-4999, 20.

* cited by examiner

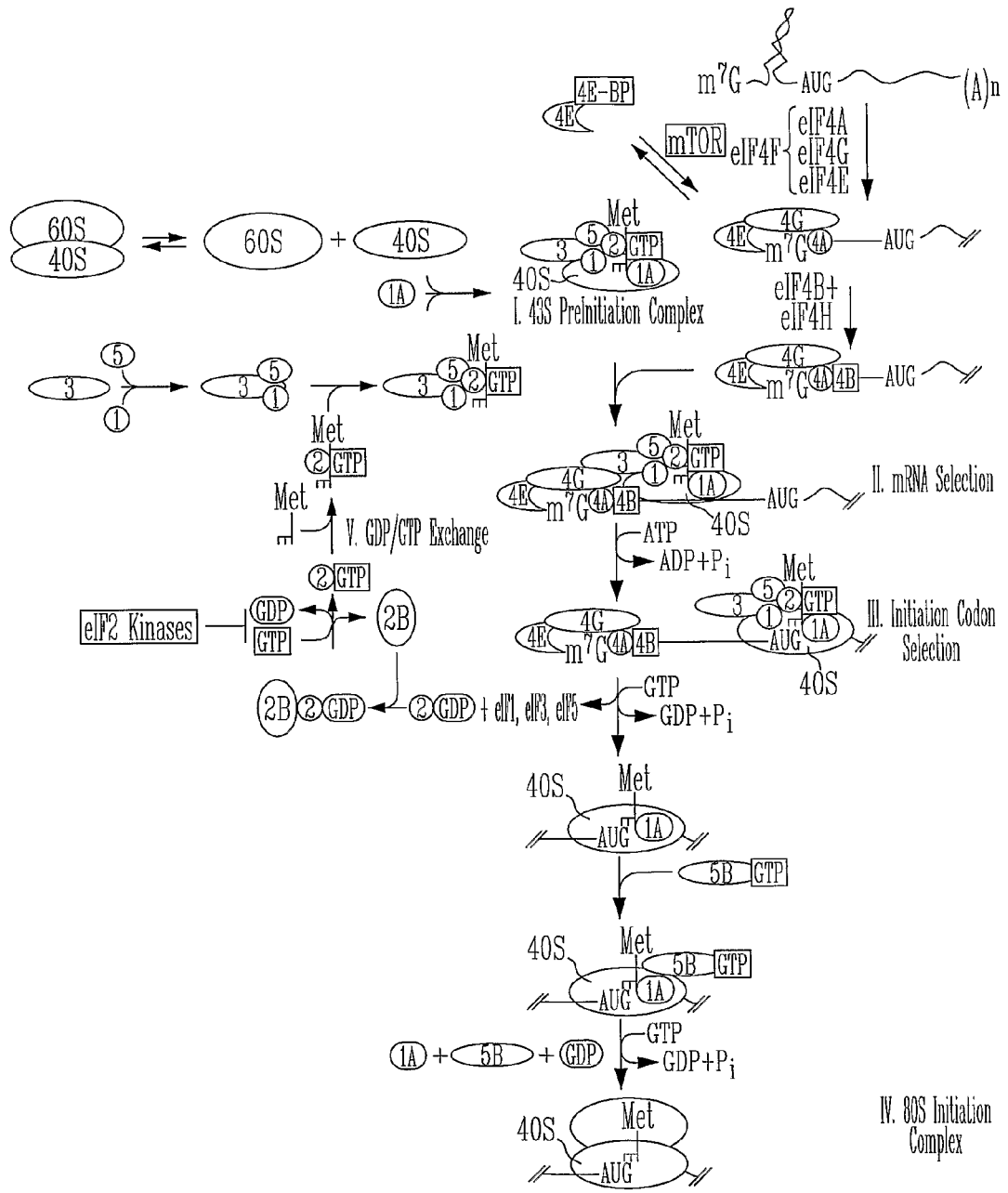

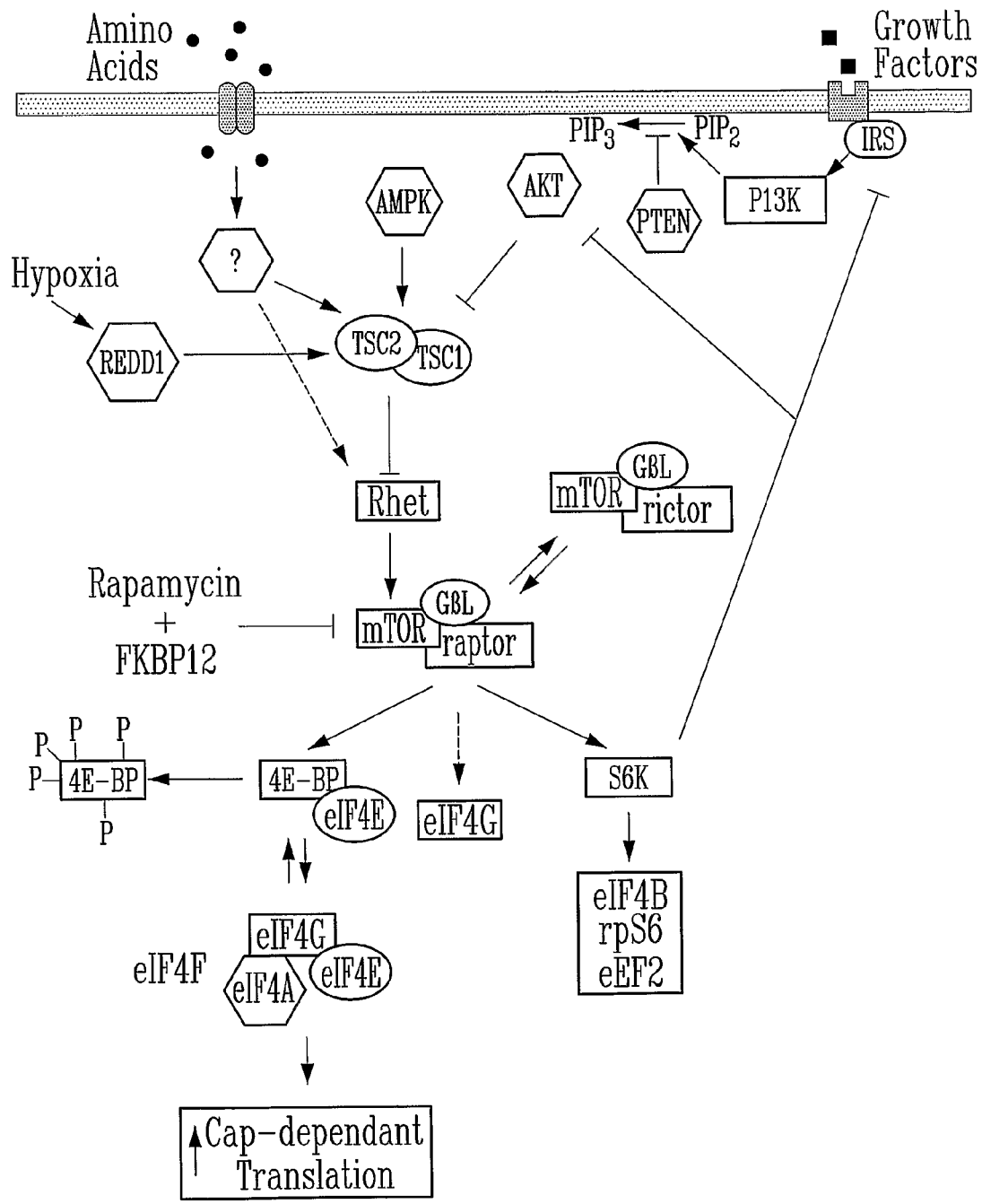

$R_1 = H \quad R_2 = R_3 = R_4 = OH$ $R_3 = OH \quad R_1 = R_2 = Cl$

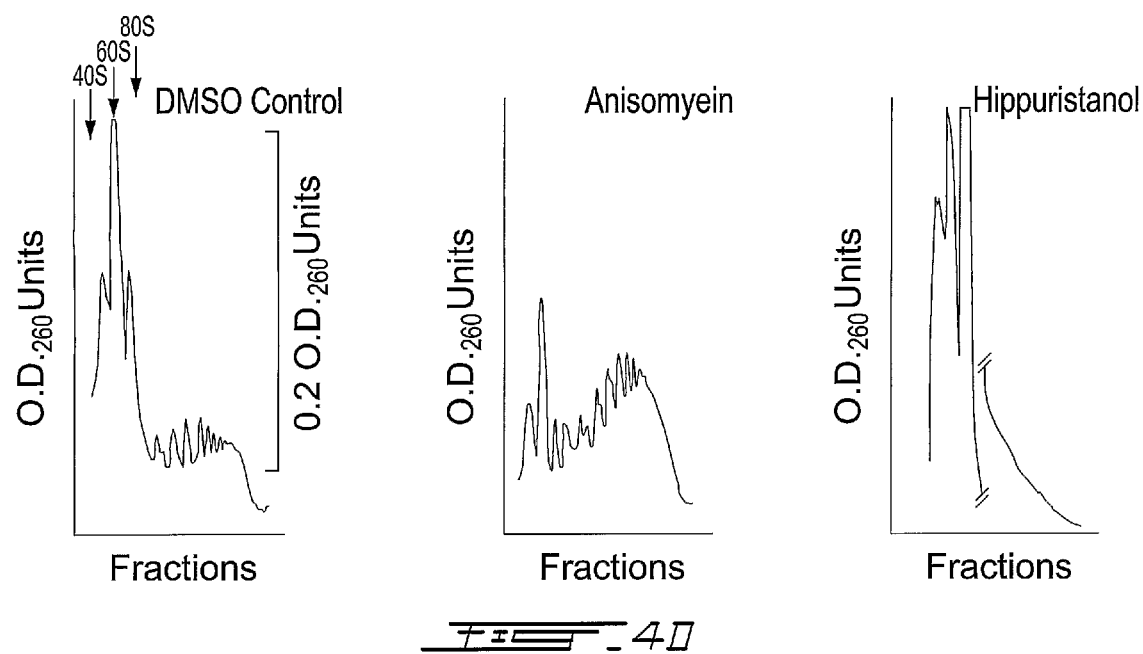

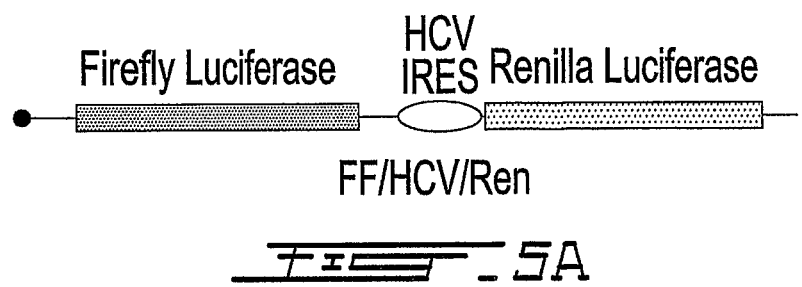
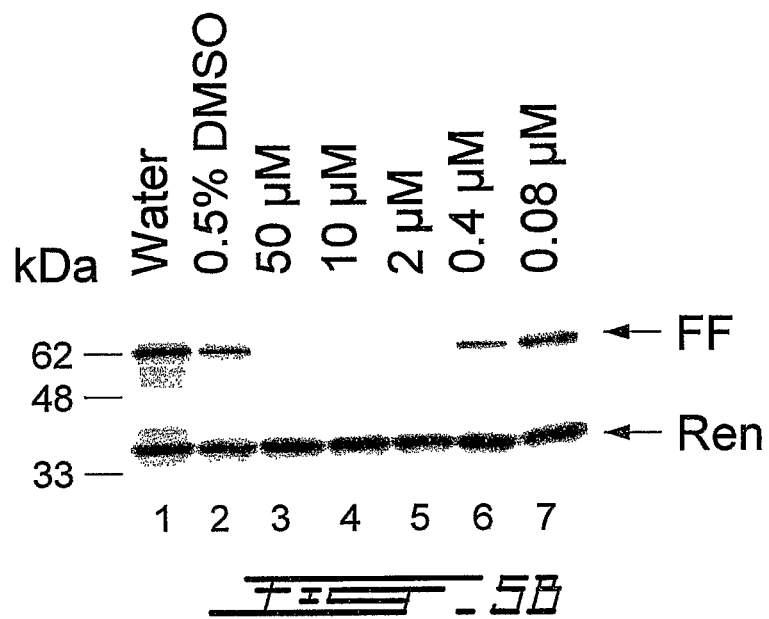
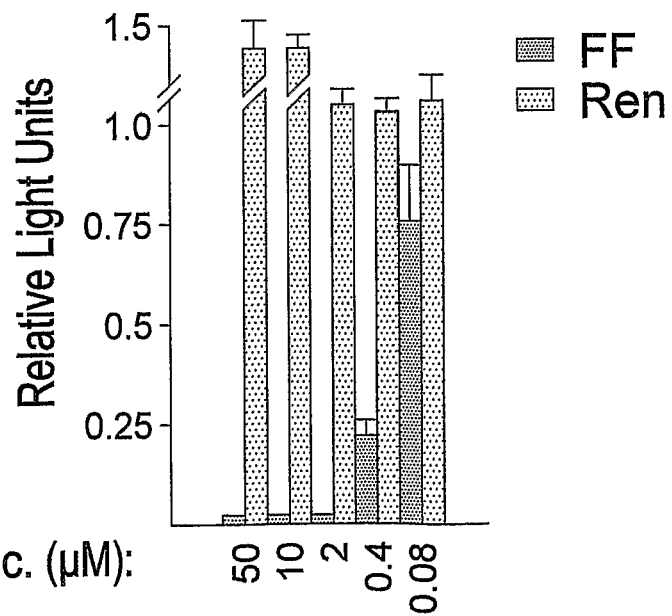

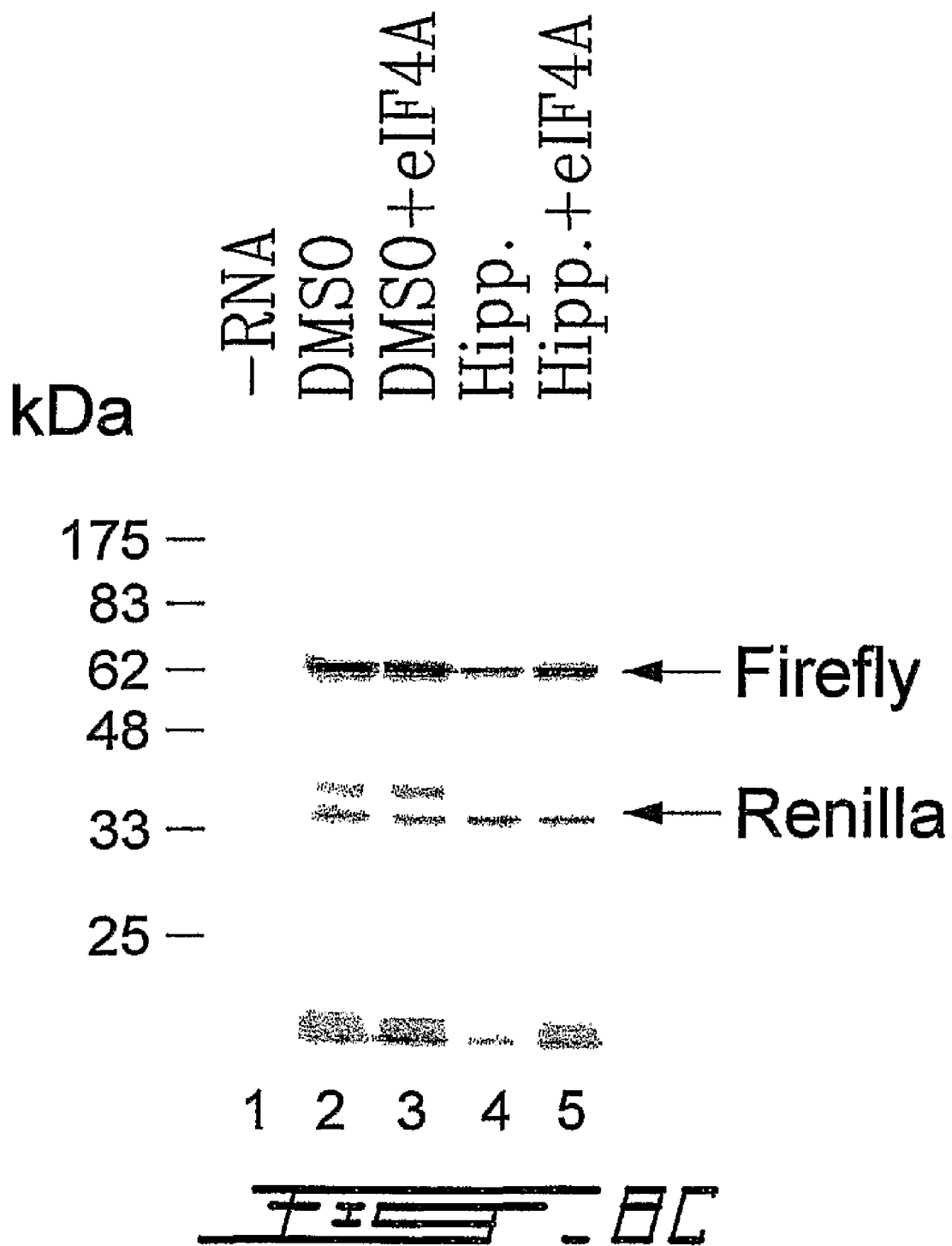

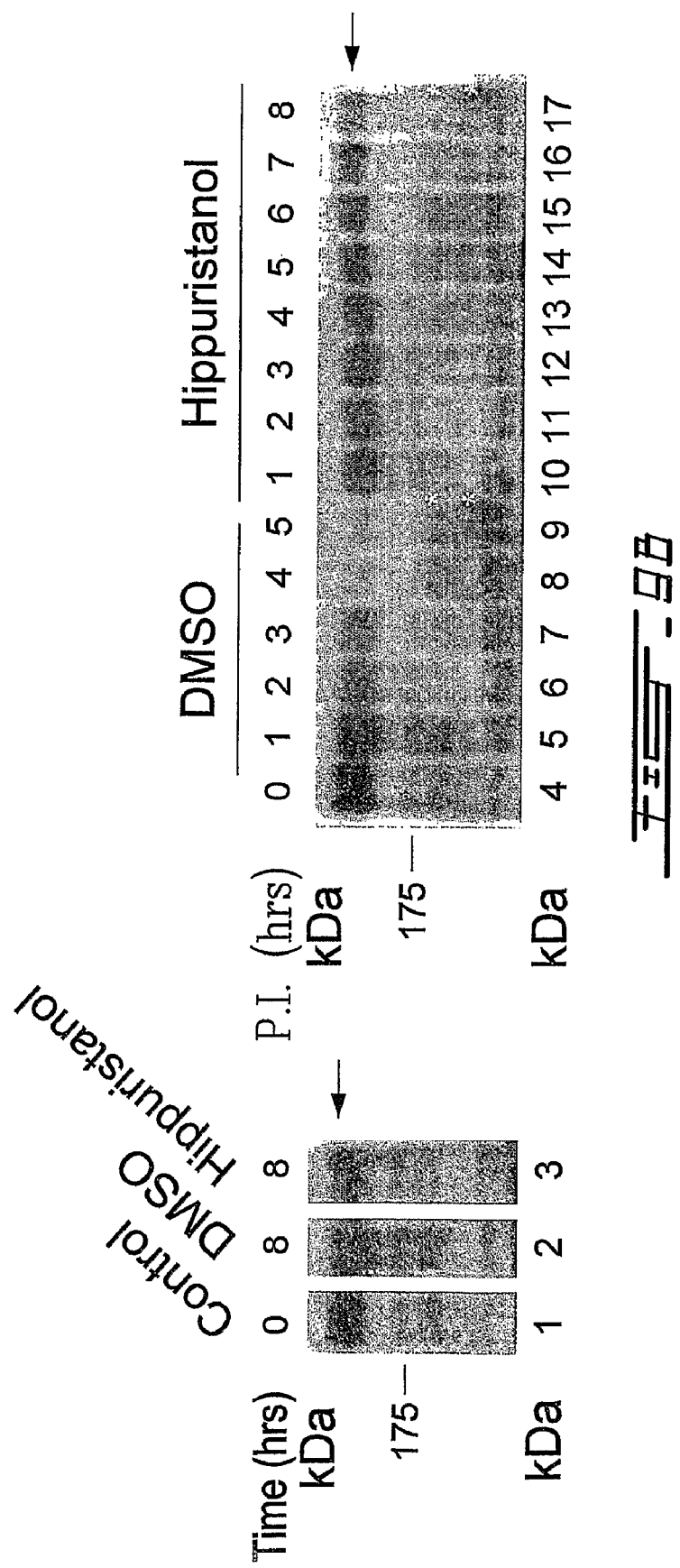

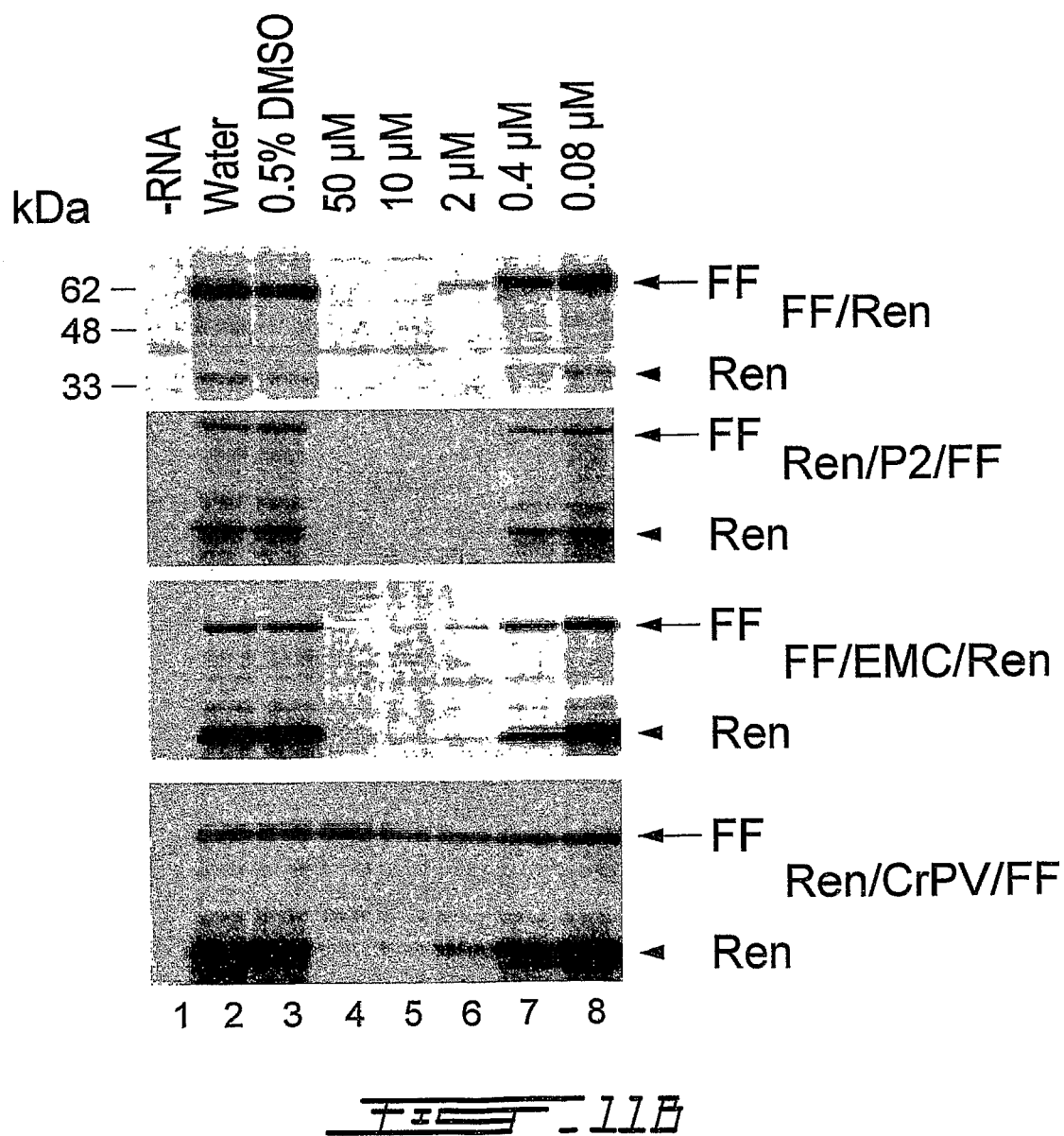

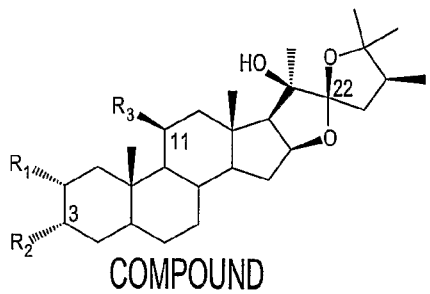

| | COMPOUND | | IC50 (Firefly) μM |
|---|---|---|---|
| 1 | Hippuristanol | R1 = H; R2=R3=OH (22R) | 0.4 ± 0.2 |
| 2 | Hippuristanol 3-acetate | R1 = H; R2 = OC(O)CH3; R3 = OH (22R) | 10 ± 1 |
| 3 | Hippuristanol 3, 11-acetate | R1=H; R2=R3=OC(O)CH3 (22R) | 64 ± 6 |
| 4 | 11-Keto-hippuristanol | R1=H; R2=OH R3=O (22R) | 9 ± 1 |
| 5 | 3,11-Keto-hippuristanol | R1=H; R2= R3=O (22R) | 52 ± 6 |
| 6 | Hippurin-1 | R1=OC(O)CH3; R2= R3=OH (22R) | 1.5 ± 3.3 |
| 7 | 2-Desacetyl-hippurin-1, 3-acetate | R1=OH; R2=OC(O)CH3; R3 = OH (22R) | 1.7 ± 0.3 |
| 8 | Desacetyl-hippurin-1 | R1= R2= R3=OH (22R) | 1.7 ± 0.4 |
| 9 | Desacetyl-hippurin-1, 2-glutarate | R1=OCO(CH2)3COOH; R2= R3=OH (22R) | 2.6 ± 1.0 |

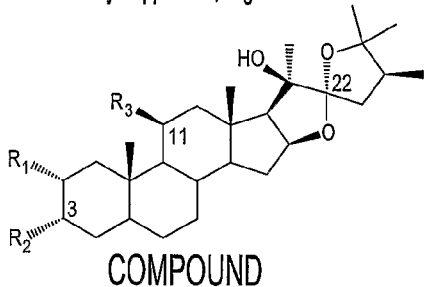

| | COMPOUND | | IC50 (Firefly) μM |
|---|---|---|---|
| 10 | Epihippuristanol | R1=H; R2=R3=OH (22S) | >100 |
| 11 | Epihippurostanol 3-acetate | R1=H; R2=OH R3=O (22S) | >100 |
| 12 | Epihippuristanol 3, 11-diacetate | R1=H; R2= R3=O (22S) | >100 |
| 13 | 11-Keto-epihippurostanol | R1=H; R2=OC(O)CH3 R3=OH (22S) | >100 |
| 14 | 3,11-Diketo-epihippurostanol | R1=H; R2=R3=OC(O)CH3 (22S) | >100 |
| 15 | Epihippurin-1 | R1=OH; R2=OC(O)CH3 R3=OH (22S) | >100 |
| 16 | 2-Desacetyl-epihippurin-1, 3-acetate | R1= R2= R3=OH (22S) | 52 ± 19 |
| 17 | Desacetyl-epihippurin-1 | R1=OCO(CH2)3COOH; R2= R3=OH (22S) | 19 ± 3 |
| 18 | Epihippuristanol-2-glutarate | R1=OC(O)CH3; R2= R3=OH (22S) | 35 ± 6 |

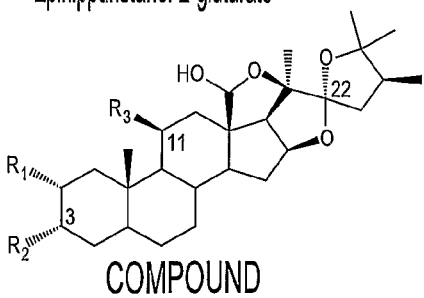

| | COMPOUND | | IC50 (Firefly) μM |
|---|---|---|---|
| 19 | Hippurostanolhemiacetal | R1=H; R2=OC(O)CH3 R3=OH (22S) | 91 ± 12 |

FIG. 12A

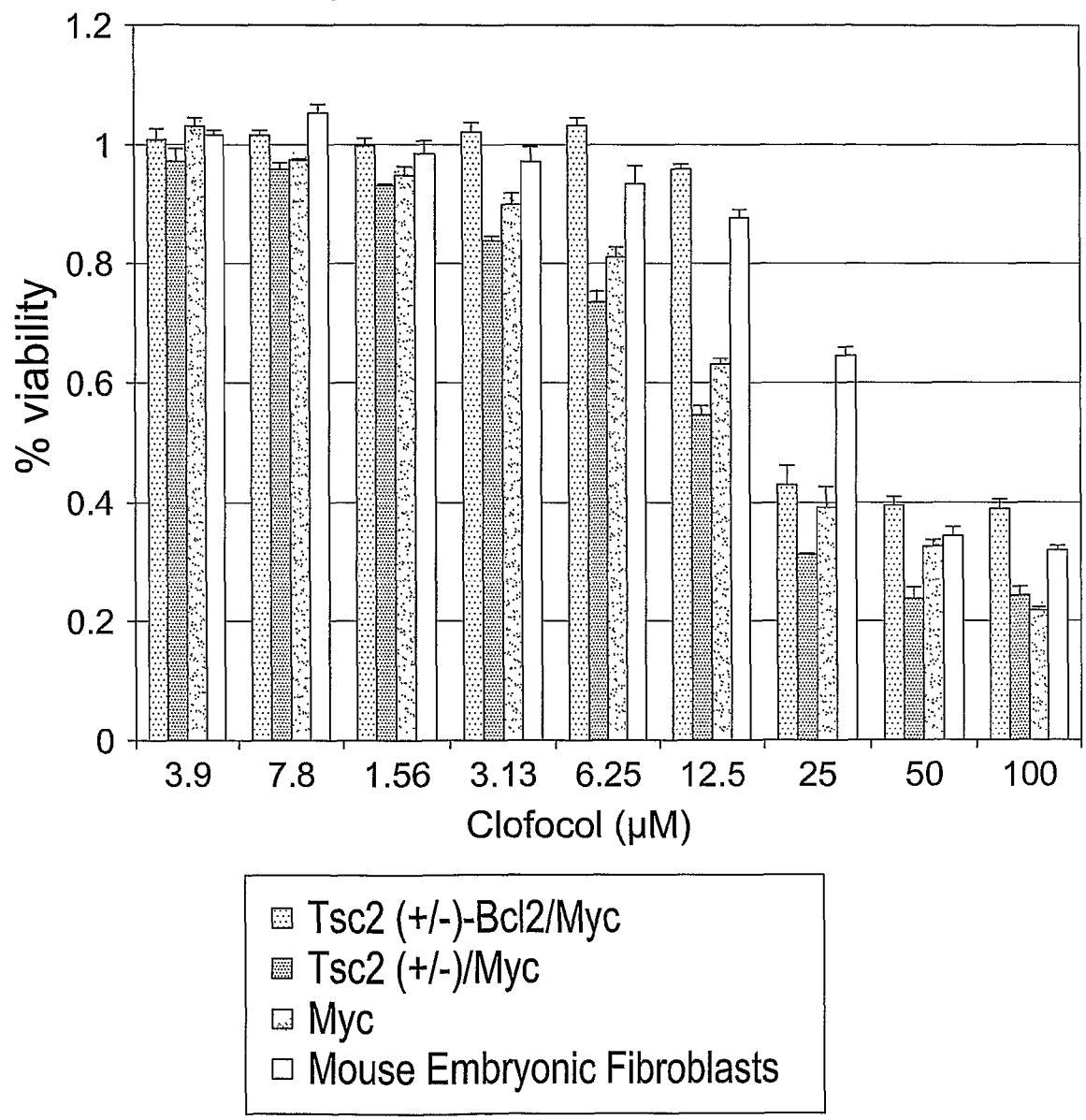

CHEMOTHERAPEUTIC AGENTS FOR INHIBITION OF PROTEIN TRANSLATION

BACKGROUND OF THE INVENTION (a) Field of the Invention

The present invention relates to inhibitors of the eukaryotic ribosome recruitment phase of translation initiation and their use as antiproliferative and/or chemotherapeutic agents and/or as adjuvants in combination therapy.

(b) Description of Prior Art

The ribosome recruitment step of translation initiation is rate-limiting and an important regulatory point whereby cellular environmental cues (e.g.—amino acid starvation, mitogenic stimulation, and hypoxia) are linked to the process of translation (18). Two distinct pathways exist for recruitment of the ribosome to the mRNA template. One mechanism is cap-dependent and is facilitated by the presence of the 5' cap structure (m7GpppN, wherein N is any nucleotide) on the mRNA. It is catalyzed by the eIF4 class of translation initiation factors and involves the recruitment of ribosomes near the 5' end of the mRNA template (18). The second mode involves ribosome recruitment in a cap-independent fashion to an internal ribosome entry site (IRES). Initiation factor requirement for internal ribosome binding varies among IRESes, with some not requiring any factors (56).

Translation initiation is the rate-limiting step of protein synthesis. In this complex process, an initiator Met-tRNAi, one molecule of GTP, and a set of initiation factors (eIF1, eIF3, eIF5, eIF1A, and eIF2) assemble on a 40S ribosome to form a 43S pre-initiation complex. Binding of the ribosome to the mRNA is generally the rate-limiting step of the entire process and occurs by one of two mechanisms: a cap-dependent mechanism (FIG. 1) and a cap-independent mechanism involving internal recruitment of the ribosome to the mRNA 5' UTR. Most translation in eukaryotes is thought to occur by a cap-dependent process involving a set of proteins that are required to recruit the ribosome to the 5' end of the mRNA template. The key complex here is eIF4F—consisting of 1) eIF4E, the cap-binding protein responsible for binding of the complex to the mRNA cap structure; 2) eIF4A, an RNA helicase required to unwind local secondary structure and thus facilitate access of the ribosome to the mRNA template; and 3) eIF4G, a modular scaffold that mediates mRNA binding of the 43S pre-initiation complex through interactions with eIF3 (which is present on the ribosome). Once bound to the mRNA, the 43S complex is thought to scan the 5' UTR, supported by ATP hydrolysis, until the appropriate AUG start codon is encountered. Mechanisms of internal initiation, bypassing the need for a 5' cap structure, have been described and the requirement for the eIF4 class of proteins varies depending on the particular mRNA under study.

Preparation of the mRNA template for cap-dependent ribosome recruitment is mediated by eIF4F, eIF4A, eIF4B, eIF4H, and ATP hydrolysis (18). The eIF4F complex is comprised of three subunits: (i) eIF4E, which binds the mRNA cap structure in an ATP-independent fashion, (ii) eIF4A, an RNA helicase that exhibits RNA-dependent ATPase activity and ATP-stimulated RNA binding activity (15) and, (iii) eIF4G, a modular scaffold that mediates mRNA binding of the 43S pre-initiation complex through interactions with eIF3. eIF4B and eIF4H cooperate with eIF4A to make its helicase activity more processive (44, 45). eIF4A exists as a free form (referred to herein as eIF4A$_f$) and as a subunit of eIF4F (eIF4A$_c$), and is thought to recycle through the eIF4F complex during initiation (37, 43, 50). It has been previously reported that when localized in the eIF4F complex, eIF4A is approximately 20-fold more active as an RNA helicase compared to its non-complexed state (38, 45). This observation has lead to the proposal that eIF4A$_c$ is the functional helicase for translation initiation (10). The helicase activity of eIF4F is thought to unwind local secondary structure in the 5' UTR of mRNAs thereby facilitating cap-dependent ribosome recruitment (37, 43, 50). The crystal structure shows that eIF4A$_f$ has a distended "dumbbell" structure consisting of two domains (6, 8, 26), which undergo conformational changes in response to RNA and ATP binding (29).

The eIF4A family comprises three members. These are characterized as eIF4AI, eIF4AII, and eIF4AIII. eIF4AI and eIF4AII exhibit 90-95% amino acid homology, are involved in translation, and appear to have similar biological activity in vitro (11, 58). eIF4AIII exhibits in the order of 65% similarity with the other isoforms and is implicated in nonsense-mediated decay (NMD) (9, 13, 35, 48). The foregoing eIF4A isoforms are members of the DEAD-box putative RNA helicase protein family. These, and related DEXD/H (where X is any amino acid) box proteins are characterized by seven highly conserved amino acid sequence motifs implicated in RNA remodeling. These proteins are involved in virtually all aspects of cellular RNA metabolism including ribosome biogenesis, transcription, splicing, translation, and mRNA degradation (for example, see http://www.helicase.net). Targeting compounds, preferably small molecules, to DEXD/H family members would provide mechanistic important insight into the properties of these proteins and help further define their roles in normal and aberrant cellular and developmental processes.

Mammalian Translation Initiation and Cancer

Disruption of one or more steps in the control of protein synthesis has been associated with alterations in the cell cycle and/or regulation of cell growth (18). Thus, proteins involved in translation initiation pathways could act as key regulators of malignant progression. There is compelling evidence supporting the concept that some translation factors are proto-oncogenes (19). Transformed cells generally show higher rates of protein synthesis compared to normal cells (20). Accordingly deregulation of protein synthesis is emerging as a major contributor to cancer progression. Overexpression of certain translation factors can lead to malignant transformation and many of the components of the translation pathways are over-expressed in cancer (19).

Cell Survival and Translation

Translational control is intimately linked to the PI3K/Akt signaling pathway. Activation of this pathway involves the production of a phospholipid, phosphatidylinositol trisphosphate [PIP$_3$], by PI3K (FIG. 2) This in turn triggers a cascade of responses that emanate from Akt activation—ranging from cell growth and proliferation to survival and motility (FIG. 10). One of several downstream targets of Akt is the TSC1 (130 kDa) and TSC2 (200 kDa) protein complex. TSC1 and TSC2 form a heterodimer that appears to be important for the stability of both proteins. TSC2 contains a GAP (GTPase Activating Protein) domain in its C terminus and binding of the TSC1/TSC2 complex to Rheb (a small ras-like GTPase) enhances the GTPase activity of Rheb, converting it to the Rheb-GDP (inactive) form. It has been speculated that Rheb might not require a guanine nucleotide exchange factor (GEF) for its activation as it is present in a high GTP bound state within cells. Subsequent activation of mTOR causes phosphorylation of 4E-BP1, liberating eIF4E from the 4E-BP/eIF4E inhibitory binary complex and stimulating protein synthesis. Complexes between eIF4E and 4E-BP1 and eIF4G have been characterized by high resolution X-ray crystallography and NMR. This pathway is up regulated in a wide range of tumor types (glioblastoma, ovarian, breast, endometrial, hepatocellular carcinoma, melanoma, digestive tract, lung, renal cell carcinoma, and lymphoid) through amplification of the p110 catalytic subunit of PI3K, loss of PTEN phosphatase activity, amplification of Akt, mutations of the tsc1 or tsc2 genes in tuberous sclerosis complex, and overexpression of eIF4E.

Inhibitors of Translation as Chemotherapeutic Agents

Several inhibitors of translation have been tested as anticancer agents, the majority of these target the elongation phase of translation. Recent experiments suggest that targeting translation initiation may be a more effective approach.

Compounds that target elongation of translation are discussed below. Sparsomycin and some of its derivatives selectively act on several different human tumors (34). Structure-activity relationship studies indicate that the anti-tumor activity is a consequence of inhibition of protein synthesis (54). Sparsomycin potentiates the cytotoxicity of cisplatin (24) and is selectively active on tumour cells without affecting human bone marrow. Unfortunately, retinotoxicity is one of the major side effects of sparsomycin derivatives in vivo (25). Tenuazonic acid has been tested in several systems for its chemotherapeutic effects. It is active in transformed cell lines (27) as well as a chemopreventive agent, preventing the formation of TPA and DMBA induced skin cancer when topically applied before the carcinogen challenge (5). Bouvardin, which inhibits EFI-dependent binding of aminoacyl-tRNA and EF2-dependent translocation of peptidyl-tRNA (59), has also been tested for its anti-neoplastic potential. It is active against murine leukemia ascites cells (10), and enhances the anti-neoplastic activity of cis-platinum (1). In combination with cis-platinum and vincristine, bouvardin does not show potentiation of activity against advance leukemias (1). Didemnin B, which blocks the translocation step of elongation (3), displays encouraging antineoplastic activity in vitro; it inhibits cell growth in human tumor stem cell assays at concentrations from 1 to 100 nM. Structure activity—studies of didemnin B indicate the same rank order in potency of translation inhibition as its anti-proliferative effects on MCF-7 cells (2). Results from phase II clinical trials suggest that didemnin B has little or no activity against advanced human cancers, possibly due to biotransformation (55). A closely related analogue of didemnin B, dehydrodidemnin 6, is ten times more active than didemnin B against murine leukemia cells (as well as in a number of human tumor xenografts) and does not exhibit the cardiotoxicity of didemnin B. Clinical trials have been undertaken with homoharringtonine, and although negative effects with solid tumors (which may be related to the dosing schedules used) have been reported, encouraging results were reported in patients with acute myeloid leukemia, myelodysplastic syndrome, acute promyelocytic leukemia, and chronic myeloid leukemia (28). Currently, structural derivatives are being generated to improve dose-limiting cardiotoxicity.

The management of Acute Lymphoblastic Leukemia (ALL) with Lasparaginase is a good example of inhibiting protein synthesis as a chemotherapeutic approach. Since transformed haematopoietic cells are often unable to synthesize sufficient asparagine for their own metabolism, they recruit it from serum. Depletion of systemic asparagine pools from the serum by administration of L-asparaginase leads to cell death (31). How asparaginase exerts its specificity on leukemic cells remains to be determined, but decreased asparagine levels are associated with inhibition of protein synthesis. One report suggests that L-asparaginase may affect signaling through FRAPImTOR by preventing phosphorylation of 4EBP1 and S6K, although this latter point needs to be verified in ALL cells.

Small molecule inhibitors which affect the initiation phase of translation and that are currently in clinical trials are derivatives of rapamycin. Tumors which harbor PTEN mutations are more sensitive to killing by rapamycin analogues, including CCI-779, RAD001 and AP23573, than their parental cells (32, 40). The activity of rapamycin is due in part to the inhibition the anti-apoptotic effects and the growth promoting activities of eIF4E. Mimosine is a plant amino acid that inhibits translation initiation through its effect on the p170 subunit of eIF3e and eIF5A (12) (4, 17). It exerts mRNA specific effects, such that the translation of ribonucleotide reductase M2 is inhibited. This is also thought to be responsible for the inhibition of DNA synthesis observed when cells are exposed to mimosine. Mimosine has been shown to induce apoptosis in human pancreatic xenografts (60). The identification of additional inhibitors of translation initiation, as described in the current proposal would provide extremely valuable tools for targeting this pathway in transformed cells. In addition to providing tools important for elucidating the mechanism by which the individual protein factors function, these small molecule inhibitors provide the starting reagents for lead development, in which the pathway of translation initiation is specifically targeted for chemotherapy.

Hippurins are cytotoxic polyoxygenated steroids isolated from the marine organism gorgonian *Isis hippuris* (52). These compounds have been reported to be cytotoxic to cell growth and the activity of a number of structurally related entities have been tested (14, 52). Analogs bearing a spiroketal ring were found to be more cytotoxic than those without this moiety, with hippuristanol being the most active. Some polyoxygenated steroids have been reported to reverse multidrug resistance (51), but the mechanistic details have remained largely unknown. Other metabolites of hippurins have been reported but have not been evaluated for biological activity (21, 42, 46, 47).

It would be highly desirable to be provided with inhibitors of eukaryotic ribosome recruitment as antiproliferative, chemotherapeutic agents and/or adjuvants.

It would be highly desirable to be provided with compounds that inhibit eIF4A-dependent translation initiation as antiproliferative and/or chemotherapeutic agents and/or adjuvants.

SUMMARY OF THE INVENTION

In accordance with the present invention there is provided inhibitors of eukaryotic ribosome recruitment as antiproliferative and/or chemotherapeutic agents and/or adjuvants.

Thus in one embodiment there is provided a use of a compound of formula I, II, III or IV to inhibit RNA translation:

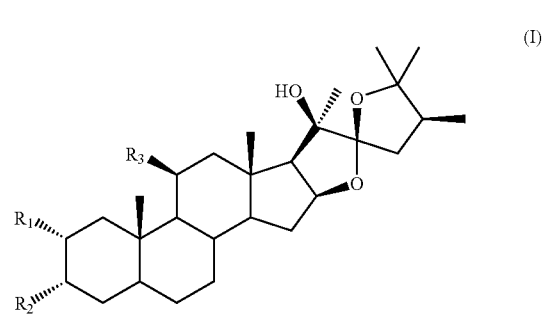

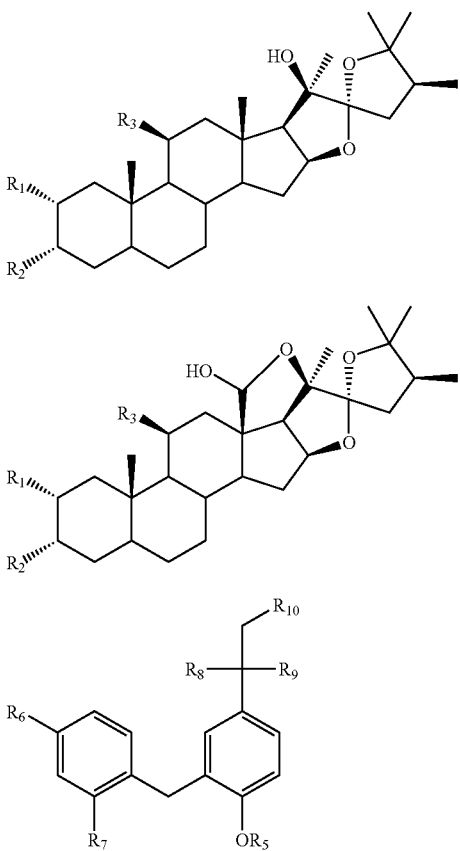

wherein
R$_1$, R$_2$ and R$_3$ are independently a hydrogen atom, a halogen atom, an oxygen atom of a ketone group, —OR$_4$, —C(O)H, —CO$_2$H, —C(O)R$_{18}$, —NR$_5$R$_6$, —SH, C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl, —(CH$_2$), C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl, C6-C$_{12}$ aralkyl, —C(O)H, or a suitable protecting group for a hydroxyl group, R$_5$ is a hydrogen atom, C$_1$-C$_{10}$ $_m$OR$_{18}$, —OC(O)R$_{18}$, —C(O)R$_{18}$, —(O)(CH$_2$)$_m$CO$_2$H, —CO$_2$R$_{18}$, —NHC(O)R$_{18}$, or —C(O)NR$_5$R$_6$, R$_4$ is a hydrogen atom alkyl, C$_2$-C$_8$ alkenyl, C$_2$-C$_8$ alkynyl, C$_3$-C$_8$ cycloalkyl, C$_4$-C$_{10}$ cycloalkenyl, C$_6$-C$_{12}$ aralkyl, —C(O)H, or a suitable protecting group for a hydroxyl group;

R$_6$ and R$_7$ are same or different and they each represent a halogen atom;

R$_8$ and R$_9$ are independently hydrogen, C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl;

R$_{10}$ is a hydrogen, C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl.

There is also provided the use of compound of formula I, II or III wherein for compound I and II:
R$_1$=H, R$_2$=R$_3$=OH;
R$_1$=H, R$_2$=OC(O)CH$_3$, R$_3$=OH;
R$_1$=H, R$_2$=R$_3$=OC(O)CH$_3$;
R$_1$=H, R$_2$=OH, R$_3$=O;
R$_1$=H, R$_2$=R$_3$=O;
R$_1$=OC(O)CH$_3$, R$_2$=R$_3$=OH;
R$_1$=OH, R$_2$=OC(O)CH$_3$, R$_3$=OH, R$_1$=R$_2$=R$_3$=OH; or
R$_1$=OCO(CH$_2$)$_3$COOH, R$_2$=R$_3$=OH;
and wherein for compound III R$_1$=H; R$_2$=OC(O)CH$_3$ R$_3$=OH.

In accordance with one aspect the present invention there is provided small molecule inhibitors of translation initiation that inhibit the RNA binding properties of eIF4A$_f$ and eIF4A$_c$, as well as the helicase activity of eIF4A.

In accordance with other aspects of the present invention there are provided pharmaceutical compositions of the preferred inhibitors of translation initiation mediated by eIF4A In accordance with other aspects of the present invention there are provided uses of the preferred inhibitors of translation initiation mediated by eIF4A.

In accordance with other aspects of the present invention there are provided methods of treating a mammal harboring a tumor in which translation is usurped.

For the purpose of the present invention the following terms are defined below.

The term "antiproliferative agents" is intended to mean a pharmacological agent that blocks cellular, parasitic, or viral growth.

The term "adjuvant" is intended to mean a pharmacological agent that could be added to a drug to enhance or aid its effect.

The term "alkyl" as used herein refers to linear or branched radicals. Examples of such radicals include, but are not limited to, methyl, ethyl, n-propyl, isopropyl, n-butyl, isobutyl, sec-butyl, tert-butyl, pentyl, isoamyl, hexyl and the like.

The term "alkenyl" as used herein refers to linear or branched radicals having at least one carbon-carbon double bond in a radical. Examples of alkenyl radicals include, but are not limited to, ethenyl, propenyl, allyl, propenyl, butenyl and 4-methylbutenyl. The term "alkenyl" include radicals having "cis" and "trans" orientations.

The term "alkynyl" as used herein refers to linear or branched radicals. Examples of such radicals include, but are not limited to, propargyl, butynyl, and the like.

The term "cycloalkyl" as used herein refers to saturated carbocyclic radicals. Examples of such radicals include cyclopropyl, cyclobutyl, cyclopentyl and cyclohexyl. The term "cycloalkyl" additionally encompasses spiro systems wherein the cycloalkyl ring has a carbon ring atom in common with the seven-membered heterocyclic ring of the benzothiepene.

The term "cycloalkenyl" as used herein refers to unsaturated carbocyclic radicals having at least one double bond. Cycloalkenyl radicals that are partially unsaturated carbocyclic radicals that contain two double bonds (that may or may not be conjugated) can be called "cycloalkyldienyl". Examples of cycloalkenyl radicals includes, but is not limited to, cyclobutenyl, cyclopentenyl and cyclohexenyl.

The terms "halo" and "halogen" as used herein refer to halogen atoms such as fluorine, chlorine, bromine or iodine. In the present invention, a haloalkyl includes radicals wherein any one or more of the alkyl carbon atoms is substituted with a halogen atom. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same or different halogen atoms. Examples of haloalkyl radicals include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" includes alkyl radicals having all hydrogen atoms replaced with fluoro atoms. Examples include trifluoromethyl and pentafluoroethyl.

The term "aryl" as used herein refers to a carbocyclic aromatic system containing one or more rings wherein such rings may be attached together in a pendent manner or may be fused. The term "aryl" includes, but is not limited to, aromatic radicals such as cyclopentodienyl phenyl, naphthyl, tetrahydronaphthyl, indanyl, biphenyl, and anthracenyl.

The term "heterocyclyl" as used herein refers to saturated, partially saturated and unsaturated heteroatom-containing ring-shaped radicals, where the heteroatoms may be nitrogen, sulfur, oxygen or combinations thereof. Preferred heterocyclyls include, but are not limited to, 3-10 membered ring heterocyclyl, particularly 5-8 membered ring heterocyclyl. Examples of saturated heterocyclic radicals include saturated 3 to 6-membered heteromonocyclic groups containing 1 to 4 nitrogen atoms (e.g., pyrrolidinyl, imidazolidinyl, piperidino, piperazinyl); saturated 3 to 6-membered heteromonocyclic groups containing from 1 to 2 oxygen atoms and from 1 to 3 nitrogen atoms (e.g., morpholinyl); saturated 3 to 6-membered heteromonocyclic groups containing 1 to 2 sulfur atoms and 1 to 3 nitrogen atoms (e.g., thiazolidinyl). Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl groups containing 1 to 4 nitrogen atoms, for example, pyrrolinyl, imidazolyl, pyrazolyl, 2-pyridyl, 3-pyridyl, 4-pyridyl, pyrimidyl, pyrazinyl, pyridazinyl, triazolyl (e.g., 4H-1,2,4-triazolyl, 1H-1,2,3-triazolyl, 2H-1,2,3-triazolyl); unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo [1,5-b]pyridazinyl); unsaturated 3 to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, isoxazolyl, oxadiazolyl (e.g., 1,2,4-oxadiazolyl, 1,3,4-oxadiazolyl, 1,2,5-oxadiazolyl); unsaturated condensed heterocyclic groups containing 1 to 2 oxygen atoms and 1 to 3 nitrogen atoms (e.g., benzoxazolyl, benzoxadiazolyl); unsaturated 5 to 6-membered heteromonocyclic groups containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl); unsaturated condensed heterocyclic groups containing 1 to 2 sulfur atoms and 1 to 3 nitrogen atoms (e.g., benzothiazolyl, benzothiadiazolyl) and the like. The term also includes radicals where heterocyclic radicals are fused with aryl radicals. Examples of such fused bicyclic radicals include benzofuran, benzothiophene, and the like.

"Heteroaryl" radicals can include, but are not limited to, fused or unfused radicals, particularly 3-10 membered fused or unfused radicals. Preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, furyl, and pyrazinyl. More preferred heteroaryl radicals are 5- or 6-membered heteroaryl, containing one or two heteroatoms selected from sulfur, nitrogen and oxygen such as thienyl, furanyl, thiazolyl, imidazolyl, pyrazolyl, isoxazolyl, isothiazolyl, pyridyl, piperidinyl or pyrazinyl. The term "heteroaryl" includes, but is not limited to, a fully unsaturated heterocyclyl. The term "heteroaryl" includes all positional isomers.

In either the "heterocyclyl" or the "heteroaryl" radical, the point of attachment to the molecule of interest can be at the heteroatom or elsewhere within the ring.

The term "aralkyl" as used herein refers to aryl-substituted alkyl radicals. Examples of such radicals include, but are not limited to, benzyl, diphenylmethyl, phenylethyl, triphenylmethyl, diphenylethyl.

All references referred herein are hereby incorporated by reference.

BRIEF DESCRIPTION OF THE DRAWINGS

Further features and advantages of the present invention will become apparent from the following detailed description, taken in combination with the appended drawings, in which:

FIG. 1. Schematic representation of cap-dependent ribosome recruitment.

FIG. 2. Schematic representation of the PI3k/Akt signaling pathways.

FIG. 15. Clofoctol Inhibits growth of tumor cell lines in culture. Lymphomas derived from Eμ-myc, Eμ-myc×Tsc2 (−/+), or Bcl2/Eμ-myc mice were exposed to the indicated concentrations of Clofoctol and cytotoxicity monitored.

DETAILED DESCRIPTION OF THE INVENTION

RNA helicases are the largest group of enzymes in eukaryotic RNA metabolism. The DEXD/H-box putative RNA helicases form the helicase superfamily II, whose members are defined by seven highly conserved amino acid motifs, making specific targeting of selected members a challenging pharmacological problem. The translation initiation factor eIF4A is the prototypical DEAD-box RNA helicase that works in conjunction with eIF4B, eIF4H, and as a subunit of eIF4F, to prepare the mRNA template for ribosome binding—possibly by unwinding secondary structure proximal to the 5' m$^7$GpppN cap structure.

In one embodiment of the invention there is provided small molecule inhibitors of eukaryotic translation initiation wherein one of such inhibitors characterized as hippurins (compound I, II and III) act by inhibiting the RNA binding and helicase activities of eIF4A.

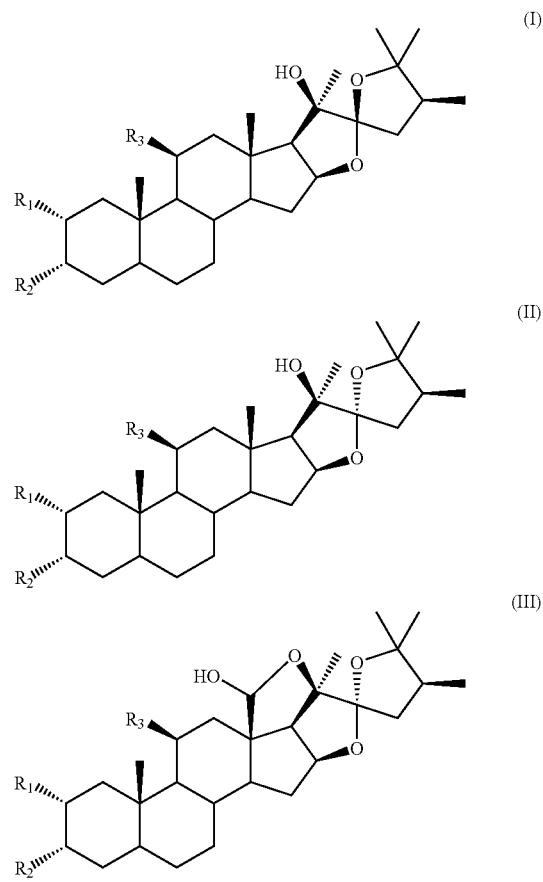

wherein
R$_1$, R$_2$ and R$_3$ are independently a hydrogen atom, a halogen atom, an oxygen atom of a ketone group, —OR$_4$, —C(O)H, —CO$_2$H, —C(O)R$_{18}$, —NR$_5$R$_6$, —SH, C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl, —(CH$_2$)$_n$C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl, C$_6$-C$_{12}$ aralkyl, —C(O)H, or a suitable protecting group for a hydroxyl group, $R_5$ is a hydrogen atom, $C_1$-$C_{10}$ $_m$O$R_{18}$, —OC(O)$R_{18}$, —C(O)$R_{18}$, —(O)(CH$_2$)$_m$CO$_2$H, —CO$_2$R$_{18}$, —NHC(O)$R_{18}$, or —C(O)NR$_5$R$_6$, $R_4$ is a hydrogen atom alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aralkyl, —C(O)H, or a suitable protecting group for a hydroxyl group;

$R_6$ and $R_7$ are same or different and they each represent a halogen atom;

$R_8$ and $R_9$ are independently hydrogen, $C_1$-$C_{10}$ alkyl, $C_2$-$C_8$ alkenyl, $C_2$-$C_8$ alkynyl, $C_3$-$C_8$ cycloalkyl, $C_4$-$C_{10}$ cycloalkenyl;

$R_{10}$ is a hydrogen, $C_1$-$C_{10}$ alkyl, $C_2$-$C_8$ alkenyl, $C_2$-$C_8$ alkynyl, $C_3$-$C_8$ cycloalkyl, $C_4$-$C_{10}$ cycloalkenyl.

There is also provided the use of compound of formula I, II or III wherein for compound I and II $R_1$=H, $R_2$=$R_3$=OH;
$R_1$=H, $R_2$=OC(O)CH$_3$, $R_3$=OH;
$R_1$=H, $R_2$=$R_3$=OC(O)CH$_3$;
$R_1$=H, $R_2$=OH, $R_3$=O;
$R_1$=H, $R_2$=$R_3$=O;
$R_1$=OC(O)CH$_3$, $R_2$=$R_3$=OH;
$R_1$=OH, $R_2$=OC(O)CH$_3$, $R_3$=OH, $R_1$=$R_2$=$R_3$=OH;
or $R_1$=OCO(CH$_2$)$_3$COOH, $R_2$=$R_3$=OH;
and wherein for compound III $R_1$=H; $R_2$=OC(O)CH$_3$ $R_3$=OH.

Figure 4A:
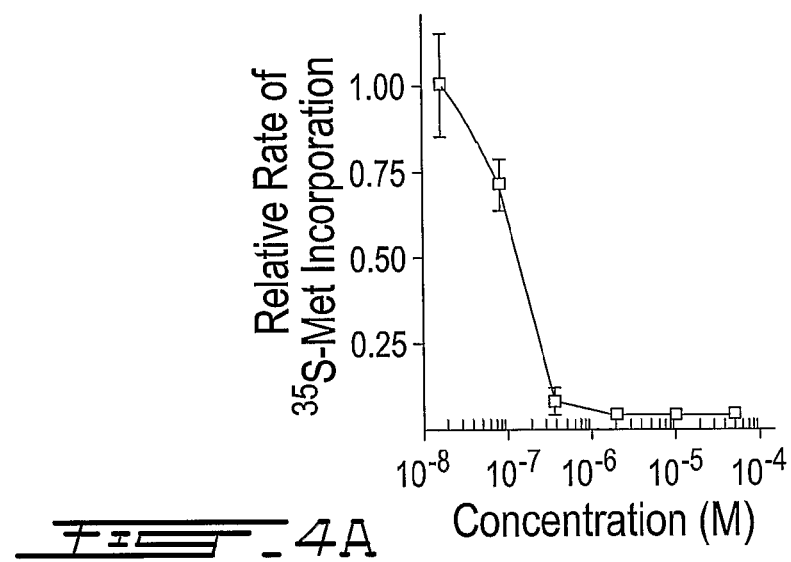
FIG. 4. Effect of hippuristanol on protein, RNA and DNA synthesis in cells. A. Relative rate of $^{35}$S-methionine incorporation as a function of hippuristanol concentration in HeLa cells. Cells were exposed to the indicated concentration of compound for 50 min., followed by a 10 min. labeling period with $^{35}$S-methionine in the presence of compound. The rate of protein synthesis (TCA precipitable cpm) obtained in the presence of compound was normalized to the rate obtained in the presence of DMSO (which was set at 1). The rate of protein synthesis in the control reactions (containing DMSO vehicle) averaged ~700,000 cpm/10 min. labeling period. Results are shown for two experiments and the error of the mean is presented. The relative rate of $^{35}$S-methionine incorporation in HeLa cells exposed to 10 µM anisomycin (positive control) for 60 min. was ~0.02 (data not shown). B. Effect of hippuristanol on protein (gray circles), DNA (open squares), and RNA (solid squares) synthesis in HeLa cells. The rate of macromolecular synthesis (TCA precipitable cpm for a 10 min. labeling period) obtained in the presence of 1 µM hippuristanol was normalized to the rate obtained in the presence of DMSO and is plotted. The results are shown for two experiments and the error of the mean is presented. The rate of protein, RNA and DNA synthesis in the control reactions (containing DMSO vehicle) averaged ~900,000 cpm/10 min, ~16,000 cpm/10 min. and 7,000 cpm/10 min labeling, respectively. The relative rate of $^{35}$S-methionine incorporation by HeLa cells exposed to 10 µM anisomycin for 60 min. (positive control for inhibition of protein synthesis) was 0.02 (data not shown). The relative rate of $^{3}$H-uridine incorporation by HeLa cells exposed to 50 µM actinomycin (positive control for inhibition of RNA synthesis) for 60 min. was 0.01 (data not shown). C. The inhibitory effect of hippuristanol on protein synthesis is reversible. HeLa cells were exposed to 1 µM hippuristanol for 60 min., after which the compound was washed off cells and fresh media (lacking compound) was added. Ten minutes before harvesting at the indicated time points, $^{35}$S-methionine was added to the media. Results shown are the average of two experiments. D. Effect of hippuristanol on HeLa cell polyribosomes. The day prior to the experiment, HeLa cells were seeded at 4×10$^{5}$ cells/10 cm petri dish. Hippuristanol (1 µM final concentration), DMSO (0.1% final concentration), or anisomycin (10 uM final concentration) was added to cells for 20 min after which the cells were washed twice with PBS, harvested with a rubber policeman and collected by brief centrifugation. The cell pellet was resuspended in lysis buffer (5 mM Tris-HCl [pH 7.5], 2.5 mM $MgCl_2$, 1.5 mM KCl, 0.5% Triton X-100, 0.5% sodium deoxycholate, 2 mM DTT), vortexed, and centrifuged for 2 min at 14,000×g. The supernatants were loaded onto 10-50% sucrose gradients prepared in 20 mM Hepes [pH 7.6], 100 mM KCl, 5 mM $MgCl_2$ and centrifuged in an SW40 at 35,000 rpm for 2 hrs. Gradients were analyzed by piercing the tube with a Brandel tube piercer, passing 60% sucrose through the bottom of the tube, and monitoring the absorbance of the material eluting from the tube using an ISCO UA-6 UV Detector. As expected, anisomycin blocked elongation and caused an accumulation of ribosomes in polysomes (16).
Figure 4B:
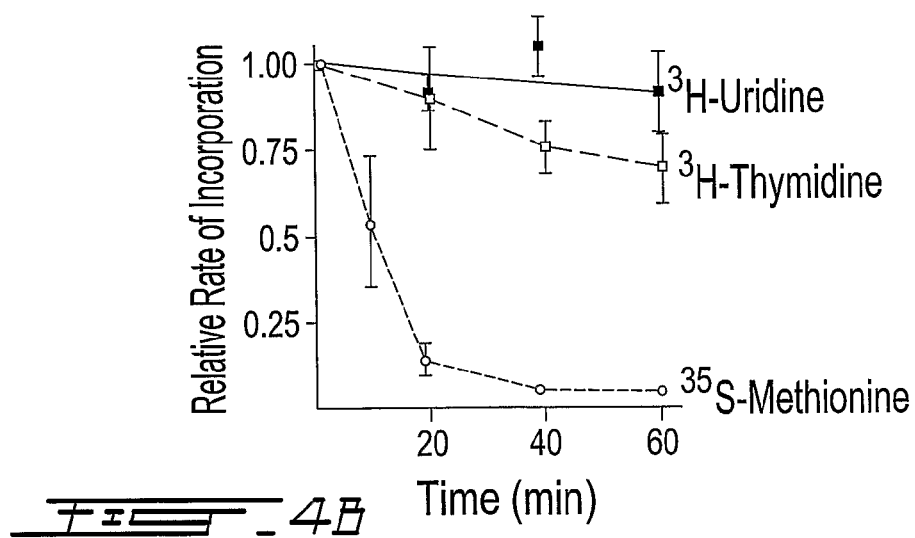
Figure 4C:
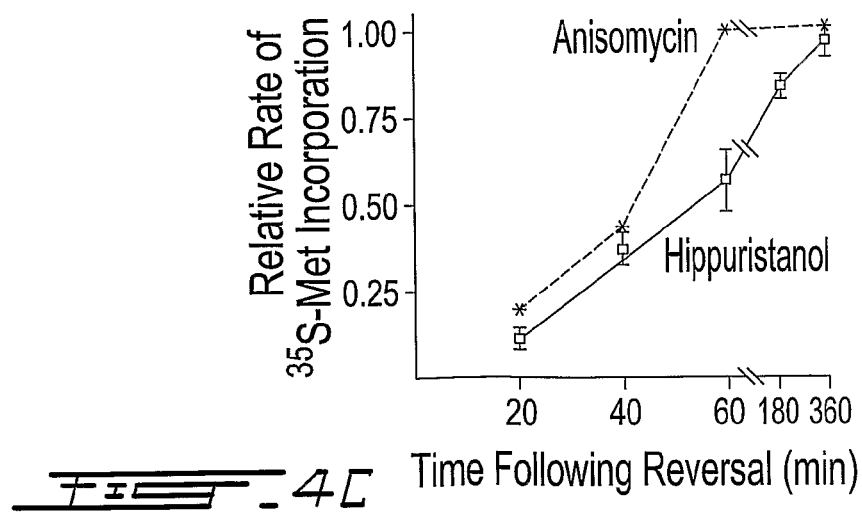
Figure 5D:
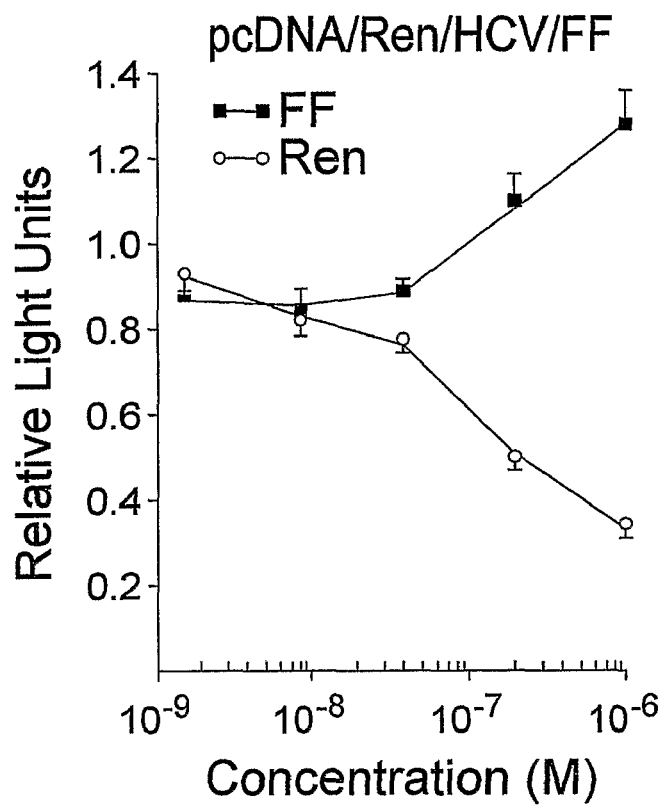
FIG. 5. Hippuristanol inhibits cap-dependent translation initiation. A. Schematic diagram of FF/HCV/Ren mRNA. B. Titration of hippuristanol in Krebs-2 extracts programmed with FF/HCV/Ren mRNA. SDS-PAGE analysis of in vitro translations performed in Krebs-2 extracts in the presence of $^{35}$S-methionine. The addition of hippuristanol and vehicle to the translation reaction is shown above the panel. C. Graphical representation of the effects of hippuristanol on the translation of FF/HCV/Ren mRNA in Krebs-2 extracts. The results shown are the average of 3 experiments. D. Effect of hippuristanol on cap-dependent and HCV IRES-mediated translation in vivo. Following transfection with pcDNA/Ren/ HCV/FF, 293 cells were incubated with the indicated concentrations of hippuristanol for 10 hrs. Luciferase activity was measured from cell extracts and is expressed relative to vehicle (DMSO) treated cells. Results are the average of 7 experiments with standard errors shown. E. Northern blot analysis of RNA isolated from cells transfected with pcDNA/ Ren/HCV/FF after incubation with hippuristanol or vehicle.
Figure 5E:
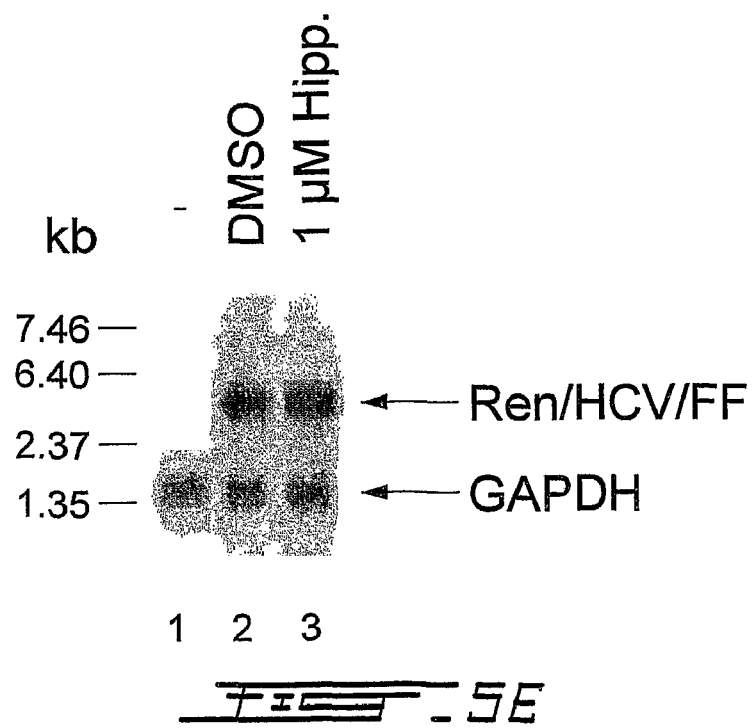
Figure 6A:
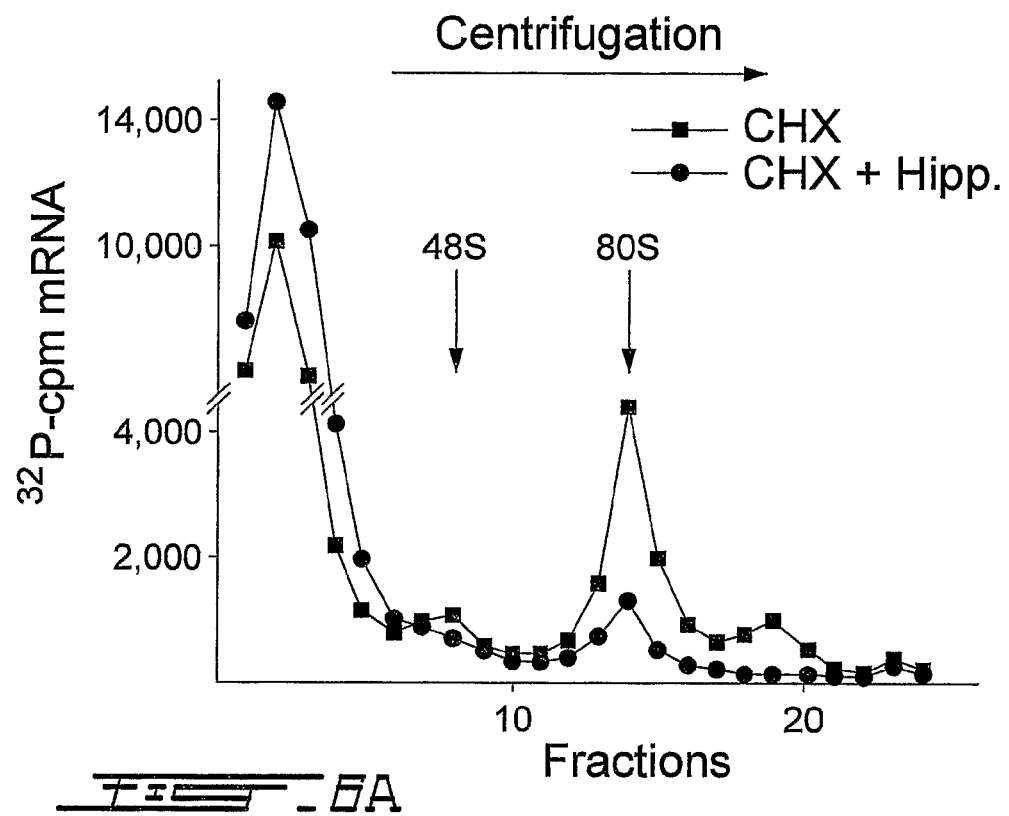
FIG. 6. Hippuristanol inhibits translation initiation. A. Hippuristanol inhibits 80S complex formation. $^{32}$P-labeled CAT mRNA was incubated in rabbit reticulocyte lysate with cycloheximide (CHX) in the presence or absence of 50 μM hippuristanol. Complexes were resolved on glycerol gradients. Total counts recovered from each gradient and the percent mRNA bound in 80S complexes were: CAT mRNA/CHX [43,498 cpm, 22% binding] and CAT mRNA/CHX+Hipp. [45,279 cpm, 5.7% binding]. B. Hippuristanol inhibits crosslinking of eIF4A$_c$ and eIF4B to capped mRNA. Initiation factors were chemically crosslinked to $^{32}$P cap-labeled mRNA in the absence (lane 2) or presence of ATP (lanes 1, 3-6), 0.6 mM m$^7$GDP (lane 3), 0.6 mM GDP (lane 4), or 50 μM hippuristanol (lane 6). Following nuclease digestion, samples were resolved by SDS-PAGE and the gel subjected to autoradiography.
Figure 6B:
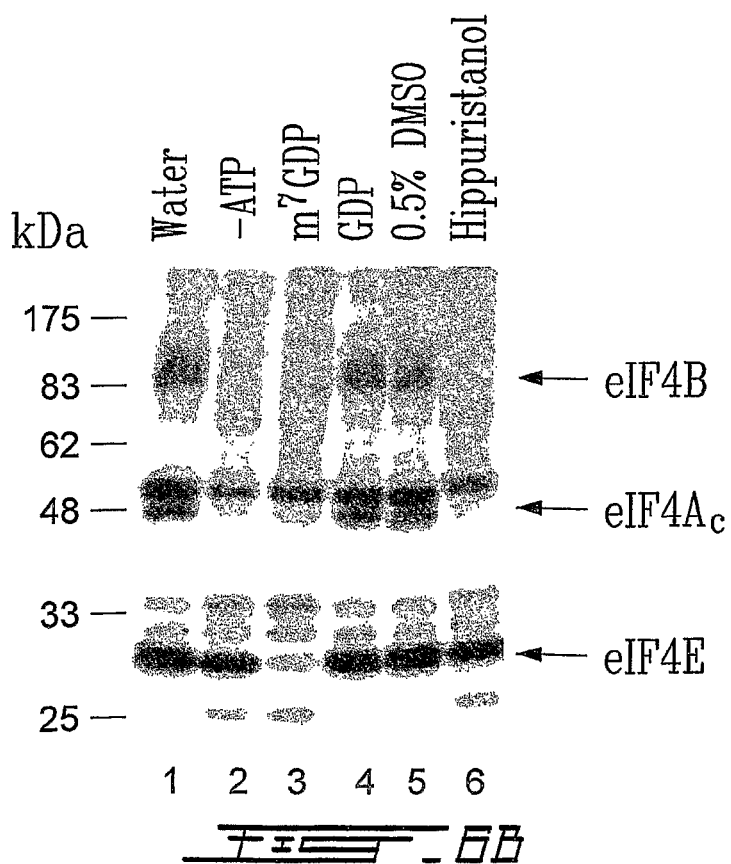
Figure 7A:
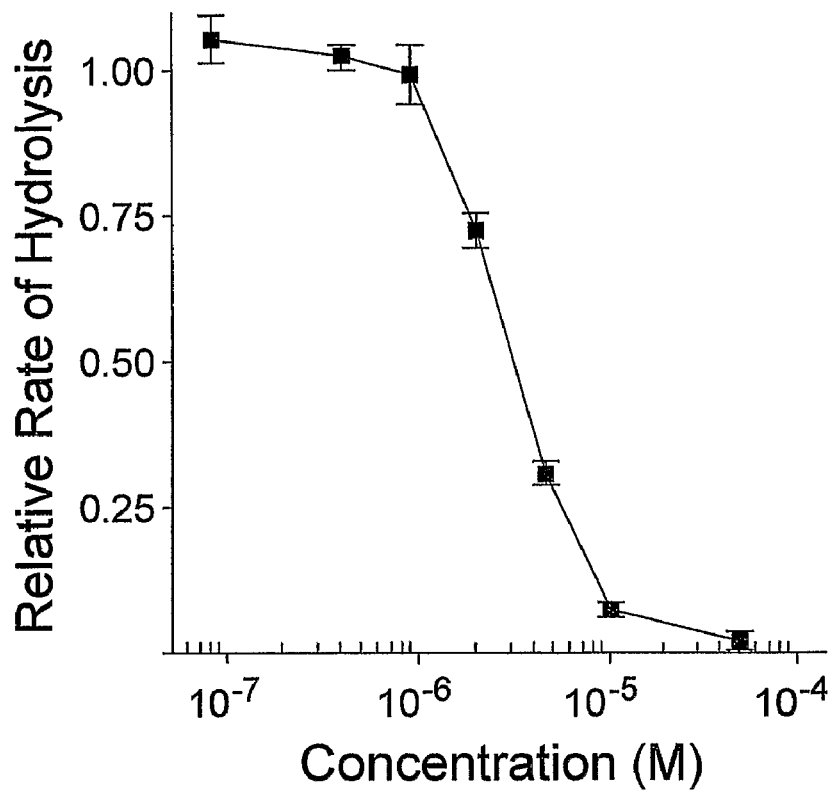
FIG. 7. Effects of hippuristanol on ATP hydrolysis, ATP binding, and RNA binding activities of eIF4A. A. Hippuristanol inhibits eIF4AI$_f$ RNA-dependent ATPase activity. The rate of ATP hydrolysis as a function of hippuristanol concentration is plotted relative to the rate obtained in the presence of vehicle (0.5% DMSO). ATP hydrolysis was measured in the presence of 2.5 μM poly (U) and monitored by thin layer chromatography. B. Hippuristanol does not affect ATP crosslinking to eIF4AI$_f$ or eIF4A$_c$. α-$^{32}$P-ATP was crosslinked to recombinant eIF4AI$_f$ (lanes 1-2) or native eIF4F (lanes 3-4) using UV light in the presence or absence of 50 μM hippuristanol. Samples were resolved by SDS-PAGE and subjected to autoradiography. C. The RNA binding activity of eIF4AI$_f$ is inhibited by hippuristanol. Oxidized $^{32}$P-cap labeled CAT mRNA was incubated with recombinant eIF4AI$_f$ in the absence (lane 2) or presence of ATP (lanes 1, 3-6), 0.6 mM m$^7$GDP (lane 3), 0.6 mM GDP (lane 4), or 50 μM hippuristanol (lane 6). Following treatment with RNase A, samples were resolved by SDS-PAGE and subjected to autoradiography. The asterisk denotes the position of migration of a ~30 kDa contaminant in the recombinant eIF4AI$_f$ preparation used as an internal loading reference. D. The RNA binding activity of eIF4A$_c$ is inhibited by hippuristanol. Oxidized $^{32}$P-cap labeled CAT mRNA was incubated with 0.7 μg of native eIF4F in the absence (lane 1) or presence (lane 2) of 50 μM hippuristanol. Following nuclease treatment, samples were resolved by SDS-PAGE and subjected to autoradiography. eIF4E crosslinking was inhibited by m$^7$GDP and eIF4A$_c$ crosslinking was ATP dependent (data not shown).
Figure 7B:
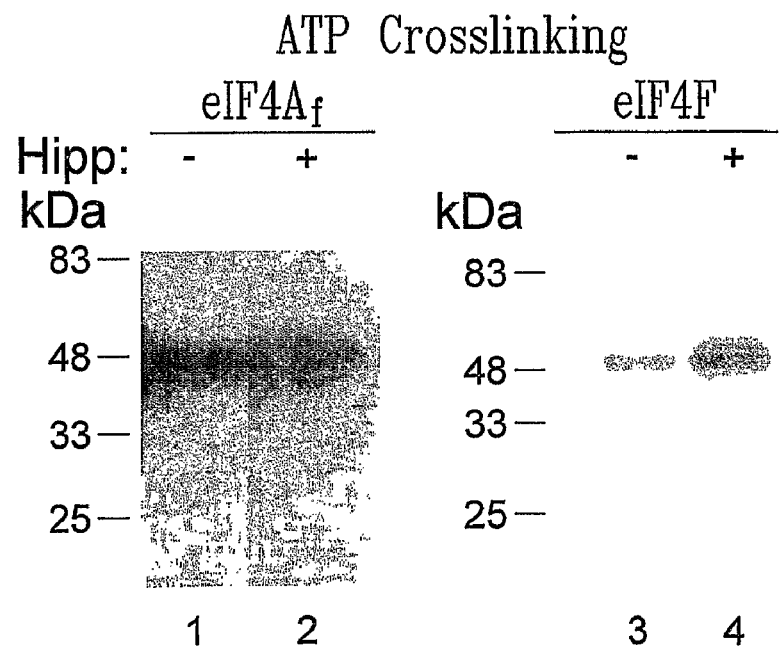
Figure 7C:
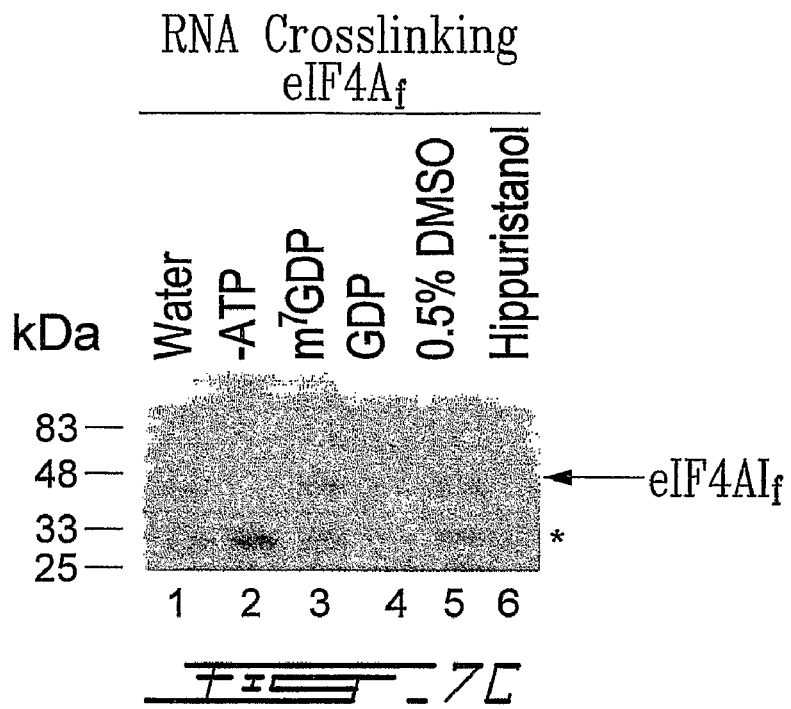
Figure 7D:
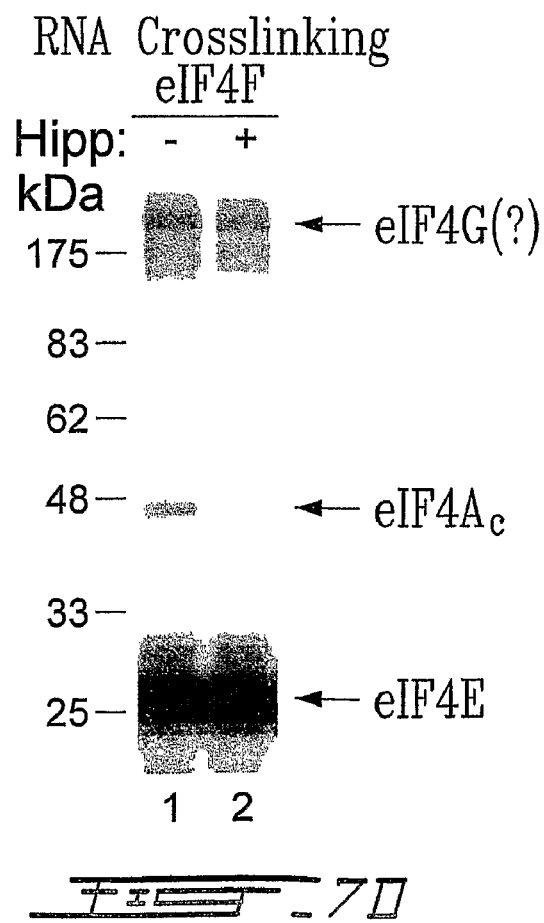
Figure 8A:
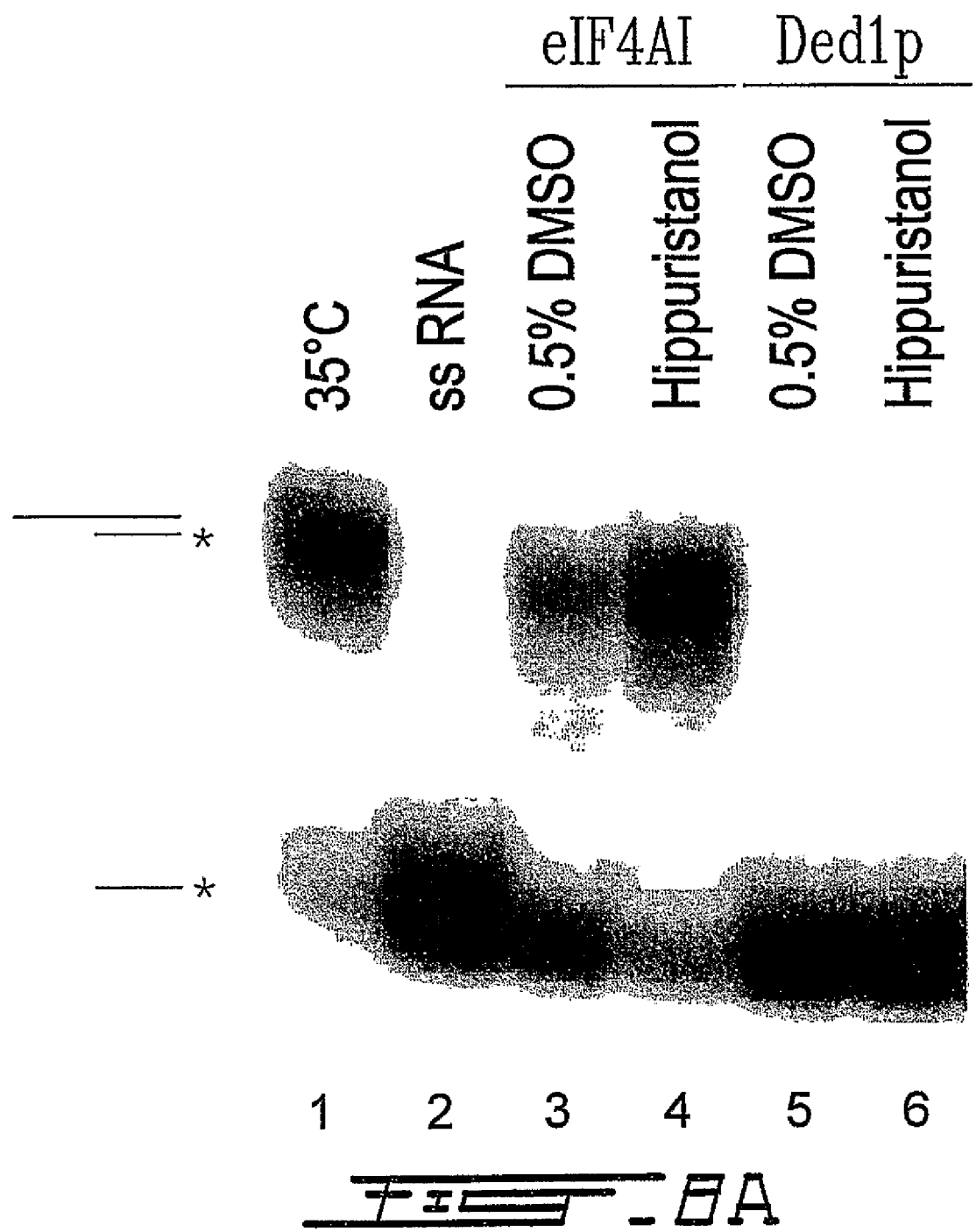
FIG. 8. Selective inhibition of eIF4A activity by hippuristanol. A. Hippuristanol inhibits eIF4AI$_f$-mediated helicase activity. Unwinding reactions were performed with RNA-1/RNA-11 duplex and recombinant eIF4AI$_f$ or Ded1p. The presence of 50 μM hippuristanol in the reaction is indicated above the panel. Reactions were resolved by electrophoresis on native 12% polyacrylamide gels and subjected to autoradiography. Double-stranded RNA duplex and single-stranded RNA molecules are schematically represented to the left of the panel. B. Hippuristanol does not inhibit in vitro splicing reactions. In vitro splicing reactions were performed with the AdML pre-mRNAs as previously described (48). AdML pre-mRNA was incubated with nuclear extracts in the presence of increasing amounts of hippuristanol (2 μM [lane4], 10 μM [lane 5] and 50 μM [lane 6]). Reaction products were resolved on 15% polyacrylamide/8M urea gels and subjected to autoradiography. The position of migration of the pre-mRNA and spliced product is denoted to the right. C. Rescue of hippuristanol-induced inhibition with recombinant eIF4AI$_f$. In vitro translations were performed in Krebs-2 extracts programmed with FF/HCV/Ren mRNA in the presence of 0.5% DMSO (lanes 2 and 3), 0.4 μM hippuristanol (lanes 4 and 5), and 1 μg recombinant eIF4AI$_f$ (lanes 3 and 5). Following in vitro translations in the presence of $^{35}$S-methionine, protein products were separated by SDS-PAGE and subjected to autoradiography. A graphical representation from three experiments is provided below. Translational efficiency was calculated relative to luciferase values obtained from control translations containing vehicle (0.5% DMSO).
Figure 8B:
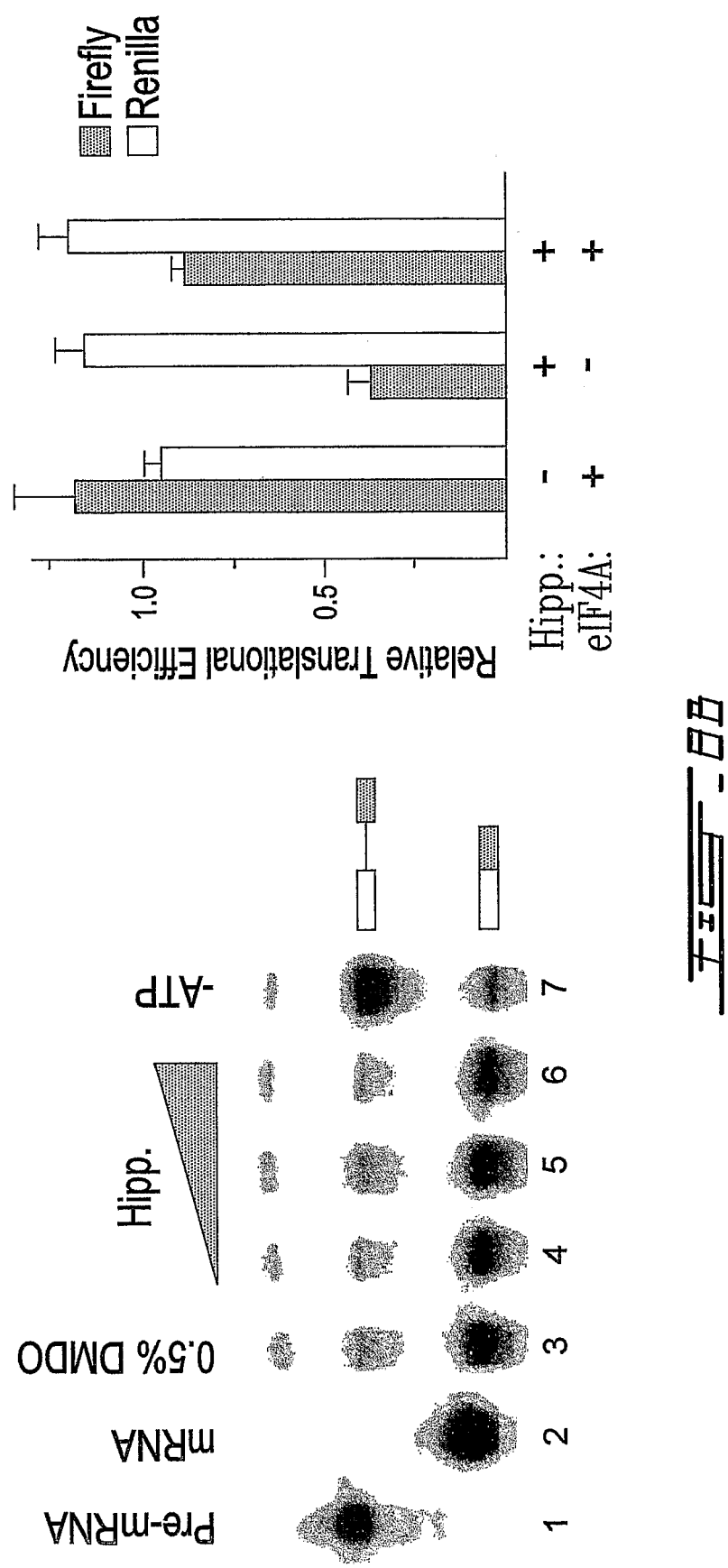

In the present invention it has been found that Hippuristanol inhibits eukaryotic protein synthesis as demonstrated by the reduction of $^{35}$S-methionine incorporation (FIG. 4). Hippuristanol exerts its effect by inhibiting cap-dependent translation initiation (FIG. 5 and FIG. 6). Furthermore it was shown that Hippuristanol inhibits eIF4AI$_f$-RNA-dependent ATPase activity and the RNA binding activity of eIF4AI$_f$ and eIF4A$_c$ (FIG. 7). The data also indicate that Hippuristanol inhibits eIF4AI$_f$-mediated helicase activity (FIG. 8).

Figure 12B:
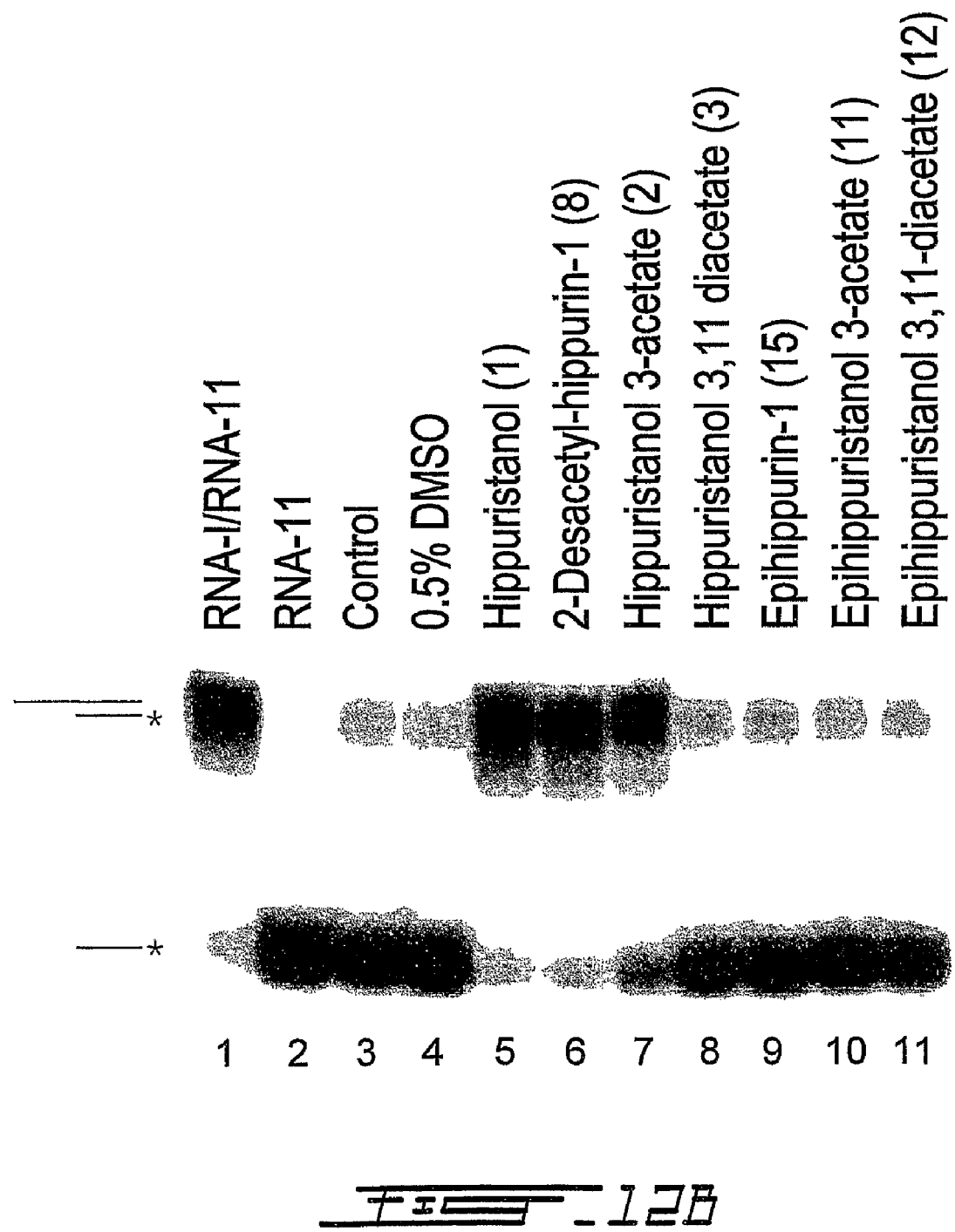
FIG. 12 Structure-Activity Relationship of hippuristanol congeners. A. The chemical structure of the hippuristanol congeners is presented along with the IC$_{50}$ determined for inhibition of cap-dependent translation in Krebs-2 extracts programmed with FF/HCV/Ren mRNA. The results shown are the average of at least 4 experiments. B. Effect of hippuristanol congeners on eIF4A1$_f$ mediated helicase activity. The hippuristanol congeners used in the reactions are indicated above the panel. Helicase reactions were resolved on native 12% polyacrylamide gels and subjected to autoradiography.

Analogs of hippuristanol exhibit similar inhibition of translation (FIG. 12). While any of the analogs can be used to inhibit translation, it will be appreciated that some are more efficient based on the IC$_{50}$ and the degree of helicase inhibition as shown in FIG. 12.

Thus, translation can be inhibited by contacting cells such as mammalian cells with the compounds mentioned above.

Figure 9A:
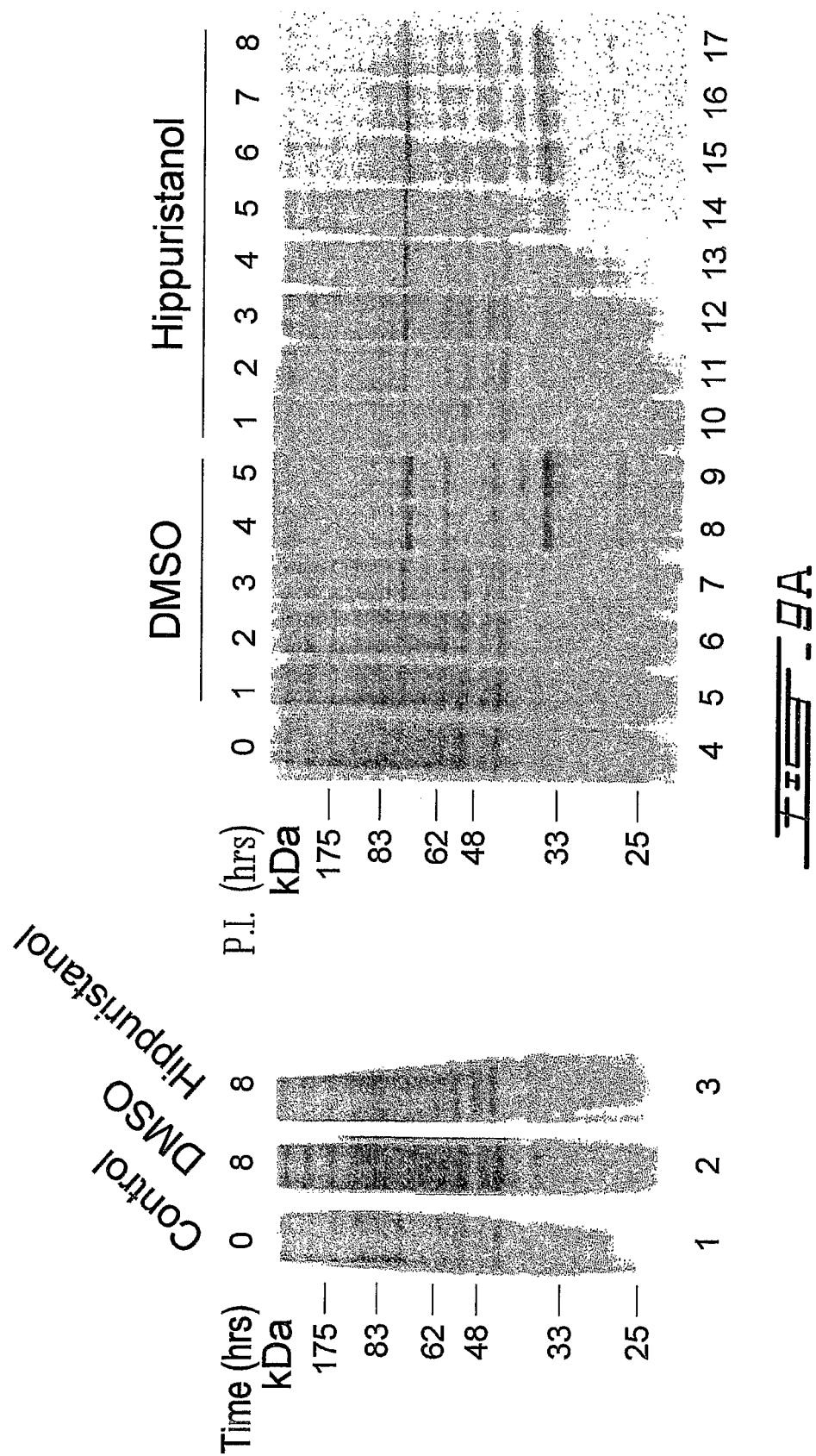
FIG. 9. Poliovirus replication is delayed by inhibition of eIF4A in vivo. A. Hippuristanol delays the onset of poliovirus proteins during infection. HeLa cells were either mock-infected (lanes 1-3) or infected with poliovirus at 2 pfu/cell (lanes 4-17) and treated with 80 nM hippuristanol (lanes 3, 10-17) or vehicle (0.5% DMSO) (lanes 1, 2, 4-9). Mock-infected cells were incubated at 37° C. for 8 hrs, while poliovirus-infected cells were incubated at 37° C. for the times indicated above the panel. Protein synthesis was monitored by metabolic labeling with $^{35}$S-methionine for ?? min. Extracts were prepared and samples resolved by SDS-PAGE and visualized by autoradiography. B. Hippuristanol delays eIF4GII cleavage following poliovirus infection. Cell extracts prepared in (A) were resolved by SDS-PAGE, transferred to PVDF membranes, and western blots performed using an anti-eIF4GII antibody. Asterisks denote the position of migration of eIF4GII cleavage products.
Figure 10A:
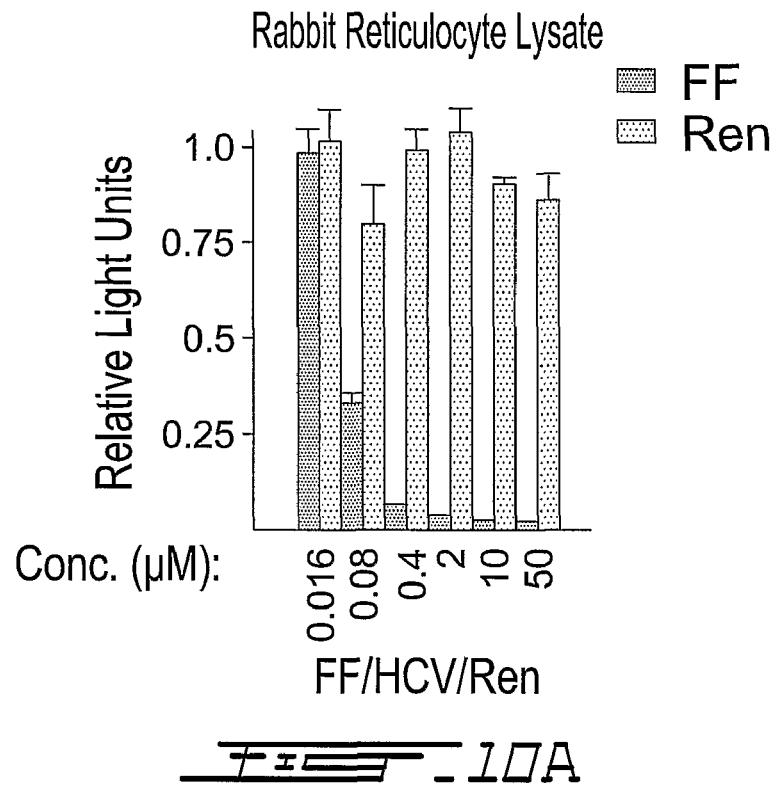
FIG. 10. Titration of hippuristanol in rabbit reticulocyte lysate (A) and wheat germ extracts (B) programmed with FF/HCV/Ren mRNA. The luciferase activities of FF and Ren were measured and normalized to the activity obtained in the absence of compound (which was set at one). The results shown are the average of 3 experiments.
Figure 10B:
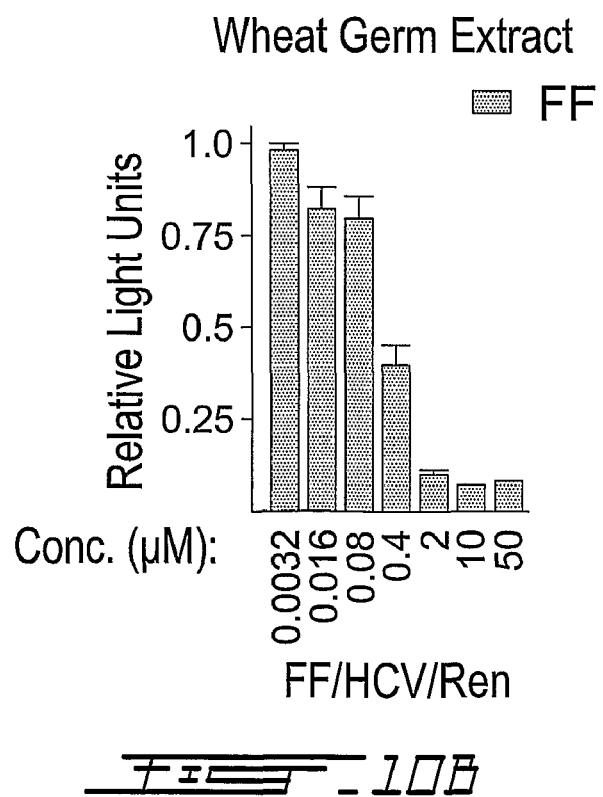

In another aspect of the invention compound I can be used to treat microorganisms infections in individuals. Hippuristanol has been shown in the present invention to inhibit the replication of microorganisms such as viruses. For example Poliovirus replication is delayed by inhibition of eIF4A in vivo (FIG. 9).

In yet another aspect of the invention it was found that compounds of molecular formula IV:

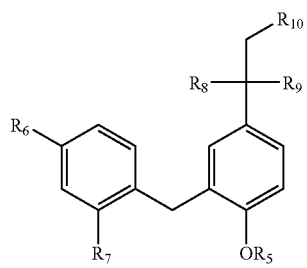

Figure 3A:
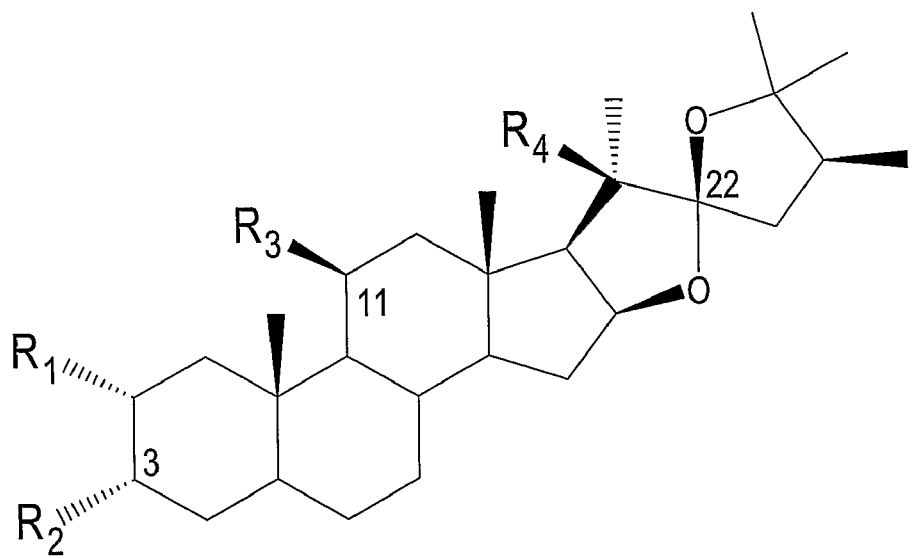
FIG. 3 Chemical structure of (A) Hippuristanol and (B) Clofoctol.
Figure 3B:
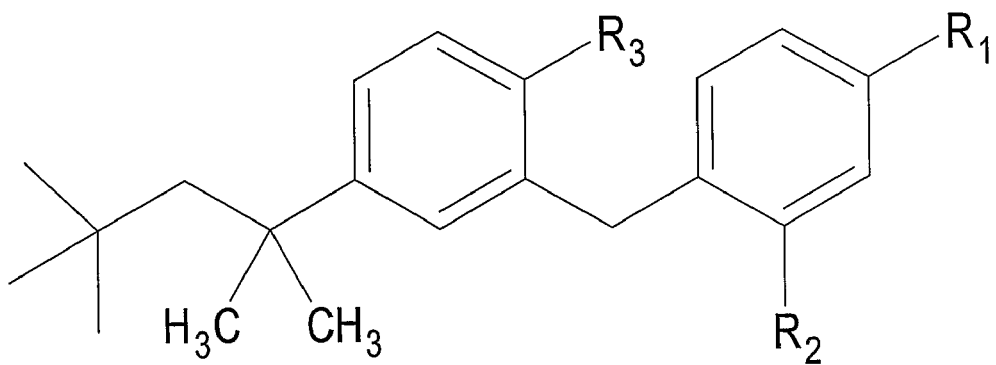
Figure 14A:
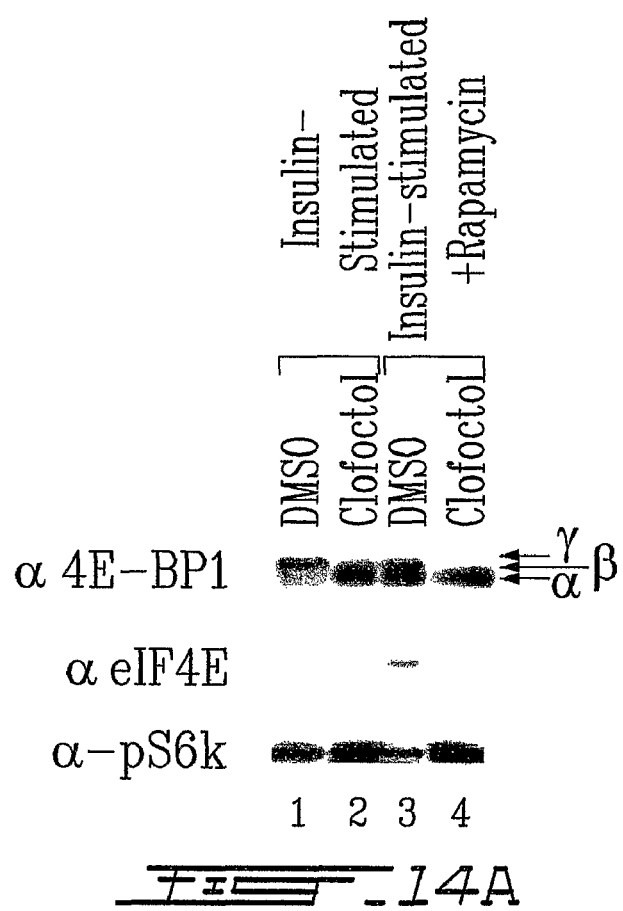
FIG. 14. (A) Western blot analysis of 4E-BP and S6K phosphorylation status in MEFs (murine embryo fibroblasts) stimulated with insulin (±rapamycin). Antibodies to pan-4E-BP and eIF4E antibodies were used. The phosphorylation status of 4E-BP is evident by a shift to a slower mobility species (shift from α to γ species). Treatment of MEF cells with clofoctol demonstrates that this compound causes dephosphorylation of 4E-BP in the presence or absence of rapamycin (upper panel). (B) Clofoctol inhibits protein synthesis in cells. MEF cells were incubated for 45 minutes in the presence of increasing amounts of clofoctol in methionine-free culture media. S$^{35}$-methionine was then added to the cell culture and incubation continued for 15 minutes. The amount of S$^{35}$-methionine incorporated into newly synthesized proteins was detected by TCA precipitation of the cell lysate following by scintillation counting. Results are expressed relative to the incorporation in the presence of 0.5% DMSO.
Figure 14B:
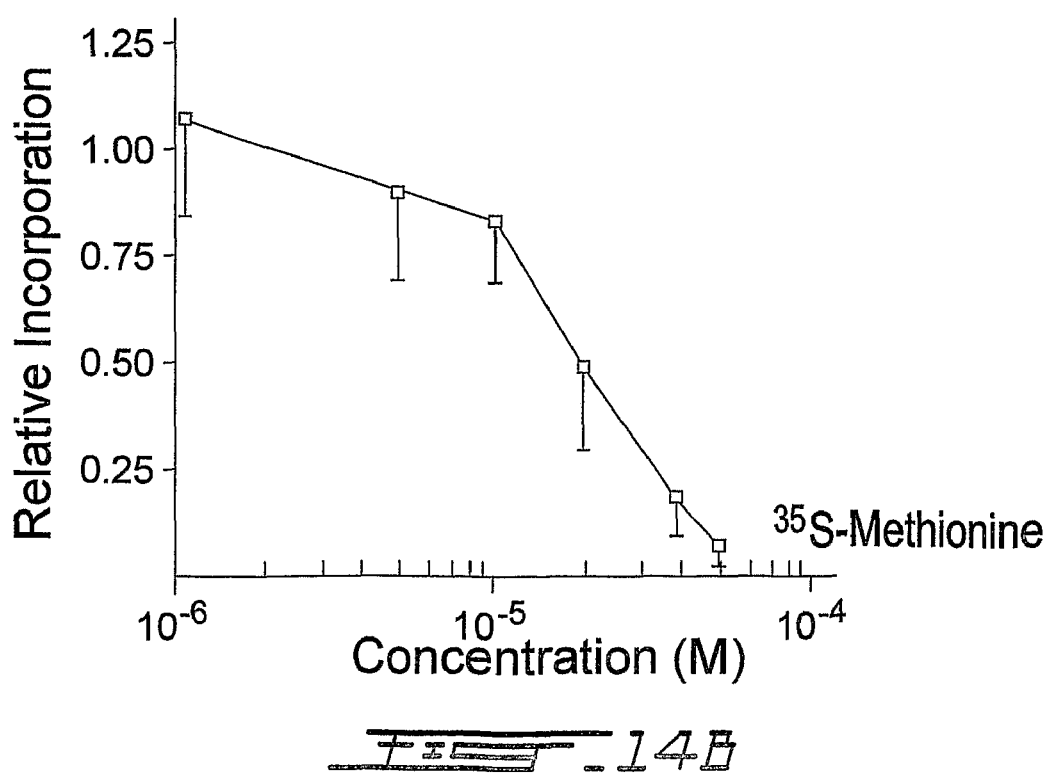

(IV)

wherein $R_5$ is a hydrogen atom, $C_1$-$C_{10}$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aralkyl, —C(O)H, or a suitable protecting group for a hydroxyl group;

$R_6$ and $R_7$ are same or different and they each represent a halogen atom;

$R_8$ and $R_9$ are independently hydrogen, $C_1$-$C_{10}$ alkyl, $C_2$-$C_8$ alkenyl, $C_2$-$C_8$ alkynyl, $C_3$-$C_8$ cycloalkyl, $C_4$-$C_{10}$ cycloalkenyl;

$R_{10}$ is a hydrogen, $C_1$-$C_{10}$ alkyl, $C_2$-$C_8$ alkenyl, $C_2$-$C_8$ alkynyl, $C_3$-$C_8$ cycloalkyl, $C_4$-$C_{10}$ cycloalkenyl, can also inhibit protein synthesis in cells (FIG. 14) and furthermore clofoctol has been shown in the present invention to inhibit the growth of tumor cell lines in culture (FIG. 15). The data show that in the PI3K/Akt/mTOR signal transduction pathway, clofoctol (structure shown in FIG. 3) affects the 4E-BP branch downstream of TOR (FIGS. 2 and 14). In the presence of rapamycin, clofoctol appears to act as an agonist of rapamycin with respect to dephosphorylation of 4E-BPs, but antagonizes rapamycin's block of S6 phosphorylation (FIG. 14A, compare lane 4 to 3). Blotting with anti-eIF4E antibodies serves as a loading control indicating that equal amounts of protein were loaded in all lanes.

Figure 13A:
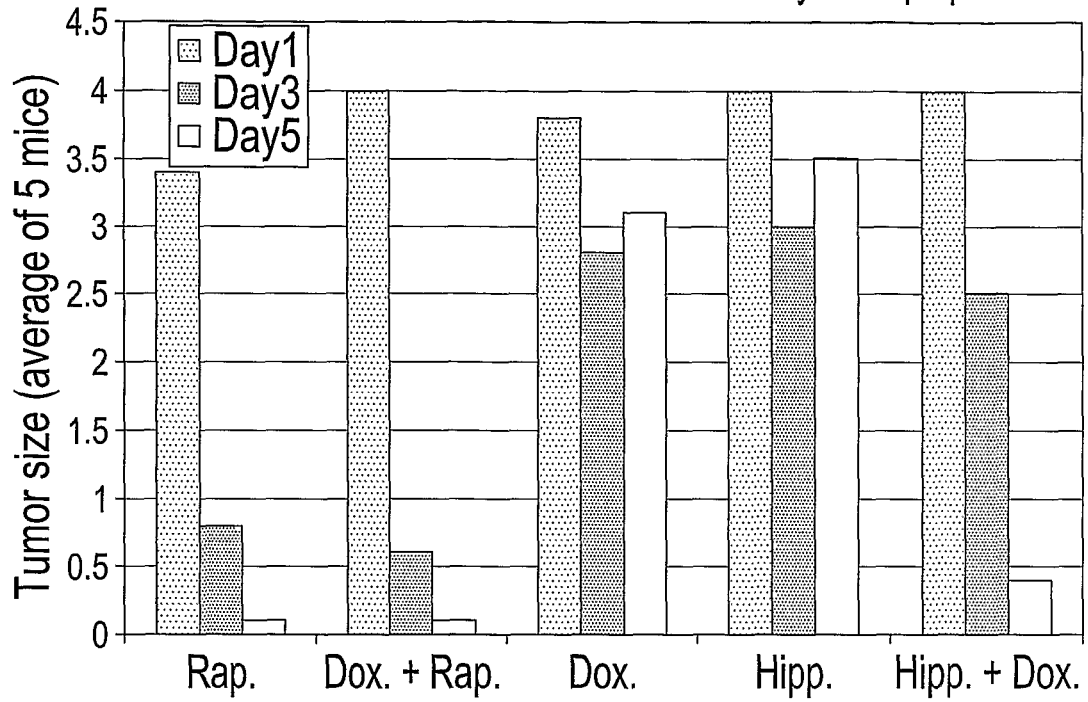
FIG. 13. Efficacy of hippurin-1 on Akt-driven Eμ-myc lymphomas when administered in combination with doxorubicin. Mice bearing Akt-driven Eμ-myc lymphomas where injected with either doxorubicin (10 mg/kg once on day 2 of 5), hippurin-1 alone (5 mg/kg every day for 5 days) or hippurin-1 and doxorubicin (hippurin-1: 5 mg/kg every day for 5 days, doxorubicin: 10 mg/kg once on day 2 of 5). Tumor size was monitored by (A) palpation (blinded study) and (B) blood smears on days 1, 3 and 5 during the treatment to assess the size of the lymphomas and the number of leukemic cells, respectively.
Figure 13B:
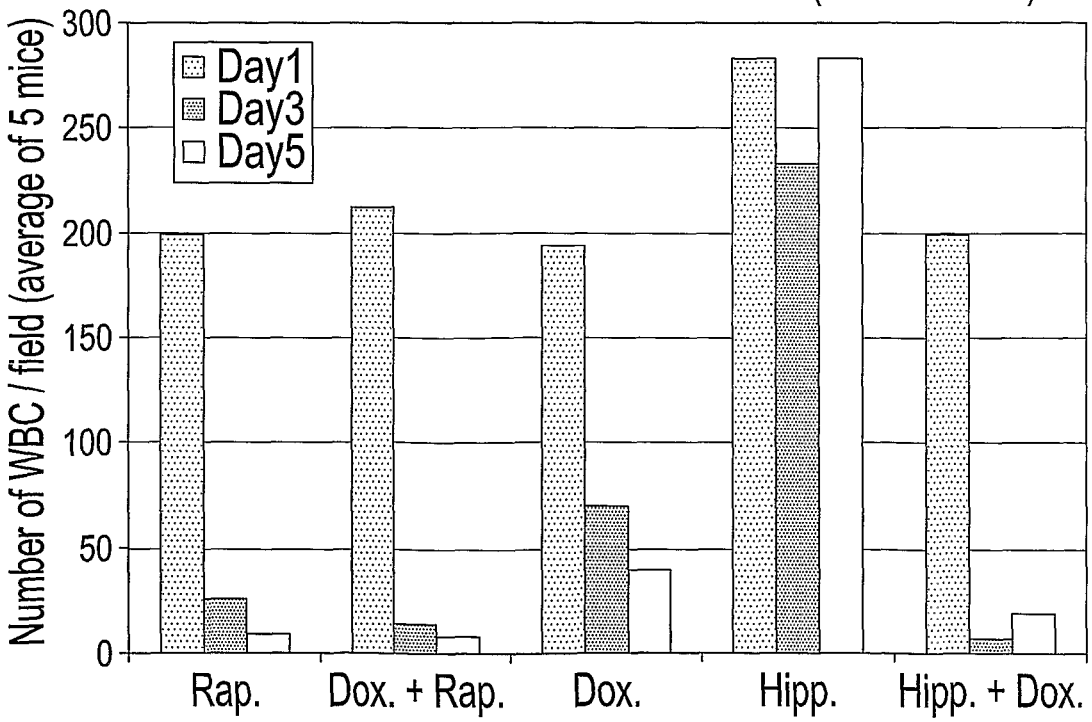

In another aspect of the invention compounds I, II, III and IV and derivatives can be used as adjuvants to chemotherapeutic agents. For example hippurin-1 can act as adjuvant to cytotoxic agents such as doxorubicin in a mouse lymphoma model (FIG. 13).

Thus compounds of formula I, II, III or IV as well as analogs can be used to treat individuals affected by hyperproliferative diseases such as but not limited to cancers, autoimmune diseases, certain skin diseases such as psoriasis or any disease that can be treated by inhibiting translation in the cells comprising the diseased tissue.

It will be appreciated that any of the compounds could be administered as a prodrug. That is to say, the administered compound (the prodrug) may undergo chemical reactions in an organism that would result in its transformation into one of the compounds described above.

The compounds of the present invention are effective over a wide dosage range, however, the exact dosage, mode of administration and form of composition depends upon the subject to be treated and is determined by the physician or veterinarian responsible for treating the subject. Generally, dosages from about 0.025 to about 200 mg preferably from about 0.1 to about 100 mg, per day may be used. Generally, the unit dosage form comprises about 0.01 to 100 mg of the compound of formula I, II III or IV, as an active ingredient together with a pharmaceutically acceptable carrier.

A carrier may take a wide variety of forms depending on the form of preparation desired for administration, e.g., oral or parenteral.

For parenteral formulations, the carrier may comprise sterile water or aqueous sodium chloride solution in combination with other ingredients that aid dispersion, such as ethanol and other pharmaceutically acceptable solvents. Injectable suspensions may also be prepared, in which case appropriate liquid carriers, suspending agents and the like may be employed.

In preparing pharmaceutical compositions in oral dosage form according to the present invention, any one or more of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, tablets or capsules may be enteric-coated or sustained release by standard techniques.

It will be appreciated that appropriate solvents for the compounds described above may also be used.

Examples of parenteral administration routes include without being limited to intravenous, intraarterial, intraperitoneal and the like.

The composition can also be formulated for topical administration.

Figure 11A:
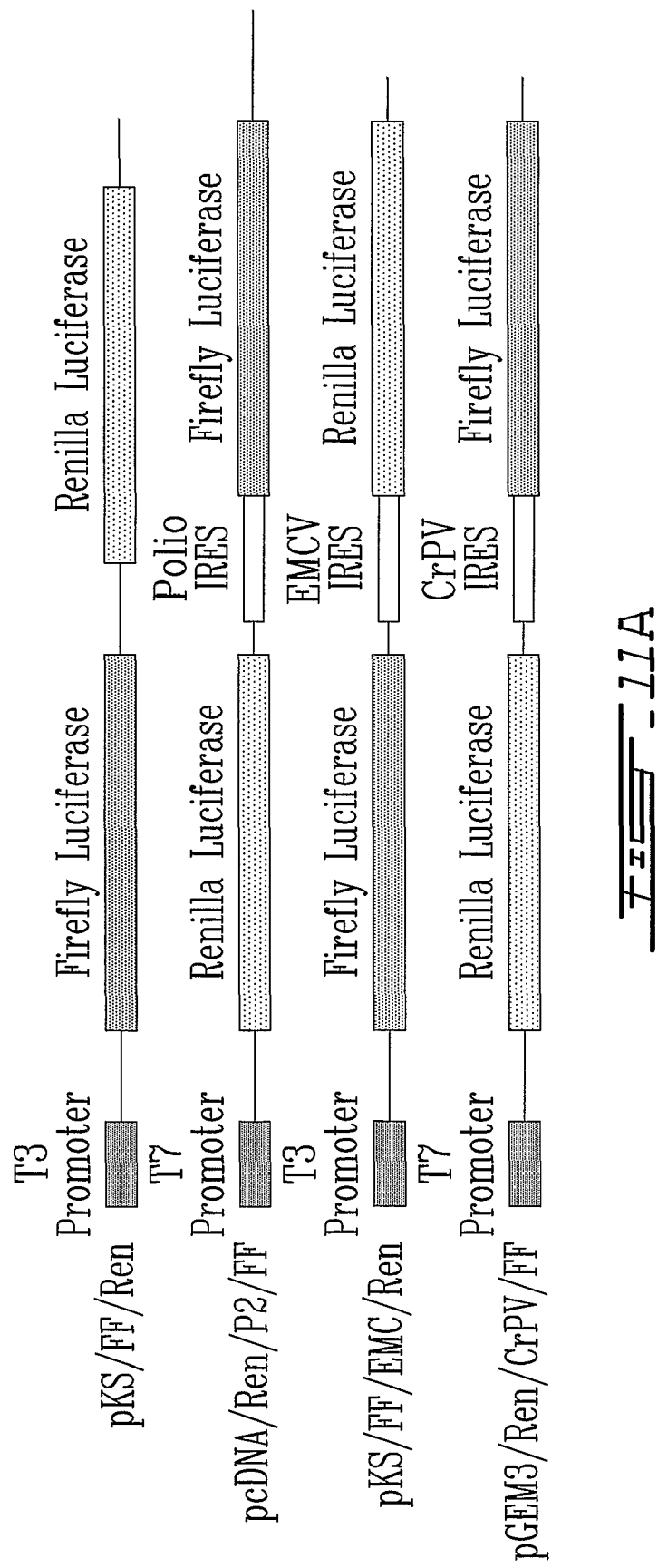
FIG. 11. Hippuristanol can distinguish between eIF4A-dependent and eIF4A-independent translation. A. Schematic diagram of bicistronic constructs used to assess eIF4A dependency of IRESes. B. Titration of hippuristanol in Krebs-2 extracts programmed with mRNA from bicistronic constructs shown in A. SDS-PAGE analysis of translation products obtained from bicistronic mRNAs translated in the presence of $^{35}$S-methionine and hippuristanol. The gels were treated with EN$^3$Hance, dried, and exposed to X-Omat (Kodak) film. The concentration of hippuristanol used in the translation mix is indicated above the panel. The position of migration of firefly and renilla luciferase protein, as well as the identity of the mRNA species translated, are indicated to the right of the panel. C. Graphical representation of the effects of hippuristanol on the translation of bicistronic mRNAs shown in A. Translations were performed in the presence of the indicated amounts of hippuristanol and at a final mRNA and K$^+$ concentration of 5 ug/ml and 100 mM, respectively. Control translations contained equivalent amounts of DMSO. The obtained luciferase activities for each different mRNA were normalized to the activity obtained in the control translations of the same mRNA species (which was set at one). The mRNA species and hippuristanol concentration used in the translations are indicated below the bar graph. Each data point represents the average of 3-7 translations and the standard error of the mean is shown.
Figure 11C:
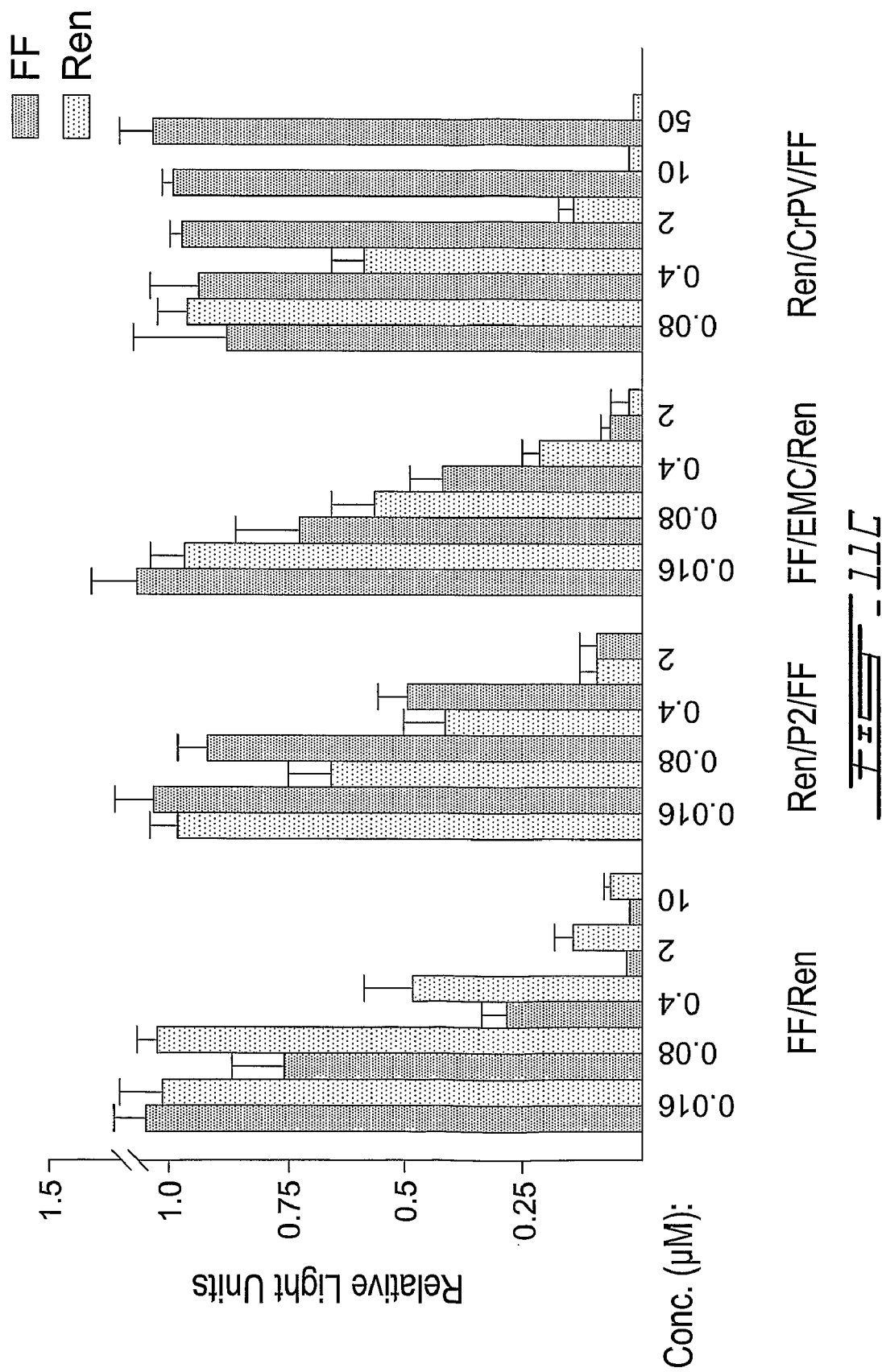

One of the advantages of Hippuristanol and its derivatives resides in the fact that its target eIF4A resides downstream of rapamycin and therefore it could be expected to be more specific than rapamycin, since the target of rapamycin, TOR, is implicated in many cellular physiological processes. Because of its specificity for eIF4A inhibition, Hippuristanol can distinguish between eIF4A-dependent and eIF4A-independent translation (FIG. 11).

The present invention will be more readily understood by referring to the following examples which are given to illustrate the invention rather than to limit its scope.

EXAMPLE 1

Materials and General Methods

Restriction endonucleases and SP6 RNA polymerase were purchased from New England Biolabs (Beverly, Mass.). 5-[$^3$H]-cytidine triphosphate (20.5 Ci/mmol), [$^{35}$S]methionine (>1000 Ci/mmol), γ-$^{32}$P-ATP (10 Ci/mmol), α-$^{32}$P-ATP (3000 Ci/mmol), α-$^{32}$P-GTP (3000 Ci/mmol), 5-[$^3$H]-uridine (22 Ci/mmol), 6-[$^3$H]-thymidine (10 Ci/mmol) were obtained from Perkin Elmer Life Sciences (Boston, Mass.). A high throughput screen performed in Krebs-2 extracts (33) was used to identify the active ethyl acetate fraction from *I. hippuris*. Hippuristanol was stored as a 10 mM stock in 100% DMSO at −70° C. Control biochemical assays always contained the same final concentration of DMSO as the parallel hippuristanol-containing reactions.

Collection of *Isis hippuris* and Extraction of Hippuristanol. Hippuristanol was purified from the gorgonian *I. hippuris* (23). A specimen of the gorgonian *I. hippuris* (2.5 kg, wet) was collected off Kohama Island, Okinawa on July 2003. The whole specimen was kept frozen until used for extraction. The material was cut into pieces and steeped in 10 L of MeOH three times. After concentration, the combined residual material was extracted with EtOAc, and the organic layer gave 27.2 g of an oil after concentration. This extract was partitioned between hexane and 50% aqueous MeOH. The aqueous MeOH layer was further partitioned with $CH_2Cl_2$. The $CH_2Cl_2$ layer was concentrated to yield 4.0 g of an oil. The hexane extract was separated by VFC (vacuum flash chromatography) on silica gel. The third fraction (2.4 g) eluted with hexane-EtOAc (5-1) was further separated on a silica gel column to give six fractions. The fourth fraction (1.1 g) from VFC was successively separated on a Sephadex LH20 column ($CH_2Cl_2$—MeOH, 1-1), a silica gel column (hexane-$CH_2Cl_2$-EtOAc), an ODS column (MeOH—$H_2O$), and finally reversed phase HPLC (MeOH—$H_2O$, 8-2) to give hippuristanol (1, 23.0 mg). The identity of hippuristanol was established by $^1$H and $^{13}$C NMR measurements and mass spectrometry (22).

Plasmid Constructions and In Vitro Translations. To generate pKS/FF/HCV/Ren, the intermediate cloning plasmid pFF/HCV/RL.pA$_{51}$ (33) was digested with BamH1 and Bg/II and inserted into the BamHI site of pKSII. For in vitro transcriptions, this plasmid was linearized with BamHI and transcribed with T3 RNA polymerase to generate FF/HCV/Ren mRNA. Construction of plasmids pKS/FF/Ren and pKS/FF/EMC/Ren have been previously detailed, and were linearized with BamHI for in vitro transcriptions with T3 RNA polymerase (33). Plasmid pcDNA/Ren/P2/FF was linearized with XhoI and transcribed with T3 RNA polymerase to generate Ren/P2/Ren mRNA (41). Plasmid pGL3/Ren/CrPV/FF was linearized with BamHI and transcribed with T7 RNA polymerase to generate Ren/CrPV/FF mRNA (57). Plasmids pGC/L (renamed from pGEM-CAT/LUC), pGC/EMC/L (renamed from pGEM-CAT/EMC/LUC), and pGC/PTV/L (renamed from pGEM-CAT/PTV/LUC) have been previously described (36, 39). Plasmid pcDNA/Ren/HCV/FF was constructed by digesting pUC18-T7-R-luc-HCV IRES-F-luc($^{53}$) with BamHI and NotI and subcloning the insert into pcDNA3.

In vitro translations were performed using Krebs-2 extracts at a final mRNA and K$^+$ concentration of 5 μg/ml and 100 mM, respectively (33). Firefly and renilla luciferase activities (RLU) were measured on a Berthold Lumat LB 9507 luminometer. Following in vitro translations in the presence of [$^{35}$S]methionine, protein products were separated on 10% polyacrylamide/SDS gels that were treated with EN$^3$Hance, dried, and exposed to X-Omat (Kodak) film. In vitro translation assays in rabbit reticulocyte lysates and wheat germ extracts were performed according to the manufacturer's instructions (Promega).

Ribosome Binding and mRNA Crosslinking. Ribosome binding assays were performed by incubating $^{32}$P-labelled CAT mRNA in rabbit reticulocyte lysate or wheat germ extracts in the presence of: 600 μM cycloheximide (CHX), 1 mM GMP-PNP, and/or 50 μM hippuristanol or vehicle for 10 min (33). Following centrifugation through 10-30% glycerol gradients (SW40; 39,000 rpm/3.5 hrs), fractions from each gradient were collected using a Brandel Tube Piercer connected to an ISCO fraction collector. Fractions of 500 μl were collected and radioactivity was determined by scintillation counting. Chemical crosslinking of initiation factor preparations to $^{32}$P cap-labeled oxidized CAT mRNA was performed under standard reaction conditions (49) containing 0.9 mM ATP. For chemical crosslinking with individual factors, 1 μg of recombinant eIF4AI$_f$ or 0.7 μg of purified eIF4F was used. After crosslinking, samples were treated with RNase A and separated on 10-15% SDS-PAGE gradient gels (initiation factor preparation) or 10% SDS-PAGE gels (individual factors). The gels were dried and exposed to X-OMAT (Kodak) film.

Recombinant eIF4AI Purification and Assays. Recombinant murine eIF4AI was expressed in *Escherichia coli* BL21 (DE3) codon+, and purified using Ni-NTA agarose and Q sepharose chromatography. ATPase assays were performed using 1 μM γ-$^{32}$P-ATP, 2.5 μM poly(U) and 4.5 μg of recombinant eIF4AI$_f$ (30). Quantifications were performed on a Fujix BAS2000 phosphoimager with a Fuji imaging screen. ATP crosslinking assays were performed with 1 μg of recombinant eIF4AI$_f$ or 0.7 μg of purified eIF4F and 2.5 μCi of α-$^{32}$P-ATP (38). Poly(U) was added to 2.5 μM where indicated. Gels were exposed to X-ray film (Kodak) at −70° C. for 12 hrs with an intensifying screen. Helicase assays were performed with the RNA-1/11 duplex and 0.4 μM recombinant eIF4AI$_f$ or 25 nM Ded1p (45). ATP was added to a concentration of 1 mM. Gels were dried and exposed to X-ray film (Kodak) at −80° C. for 12 hrs with an intensifying screen.

Cell Transfections. 293 cells were maintained in DMEM media supplemented with 10% fetal calf serum. The day before calcium phosphate transfection, cells were seeded at 3×10⁶ cells/10 cm dish. Following transfection with pcDNA/Ren/HCV/FF, 293 cells were incubated for 10 hrs with hippuristanol or vehicle before harvesting, and were collected 48 hrs post-transfection. Luciferase assays were performed with the dual luciferase assay kit according to manufacturer's instructions (Promega). Probes for Northern blots were produced using the Readiprime kit (Amersham).

Poliovirus Infections. The day prior to infection, 4×10⁵ HeLa cells were plated per 35 mm dish. For absorption, cells were washed with PBS, followed by the addition of the Mahoney strain of poliovirus type 1 (2 pfu/cell) in serum free D-MEM containing vehicle or hippuristanol. Cells were incubated at room temperature for 30 minutes with gentle rocking, after which the media was removed. Cells were washed with PBS, fresh media containing 10% fetal bovine serum was added, and cells were incubated at 37° C. for the indicated times. Thirty minutes before harvesting, [$^{35}$S]methionine was added (50 µCi/mL) to the media. Mock-infected cells were incubated at 37° C. for 8 hrs, while poliovirus-infected cells were incubated at 37° C. for the times indicated above the panel. For harvesting, cells were washed with PBS and extracts prepared in PLB (0.1% SDS, 0.5% sodium deoxycholate, 1% Triton X-100, 1 mM PMSF) (7).

Isolation of Steroids 6, 8, 10, 15, 17, and 19.

The crude EtOAc extraction obtained from the MeOH concentrate from *I. hippuris* was partitioned between hexane and 50% aqueous MeOH. The hexane layer was concentrated to give 18.3 g. The aqueous MeOH layer was partitioned with $CH_2Cl_2$ and the $CH_2Cl_2$ layer concentrated to yield 4.0 g of an oil. Both hexane and $CH_2Cl_2$ extracts were used to separate hippuristanol congeners. The hexane extract was first separated by VFC (vacuum flash chromatography) on silica gel. The third fraction (2.4 g) eluted with hexane/EtOAc (5:1, v/v) was further separated on a silica gel column to give six fractions. The fourth fraction (89.7 mg) eluted with $CH_2Cl_2$/EtOAc (1:1, v/v) gave precipitates that were found to be compound 19 (73.5 mg). The fourth fraction (1.1 g) eluted with hexane/EtOAc (1:1, v/v) from VFC was successively separated on a Sephadex LH20 column ($CH_2Cl_2$/MeOH, 1:1, v/v), a silica gel column (hexane/$CH_2Cl_2$/EtOAc/MeOH, 1:1:0:0, 5:1:0:0, 1:1:0:0, 1:5:0:0, 0:1:0:0, 0:5:1:0, 0:1:1:0, 0:1:5:0, 0:0:1:0, 0:0:10:1, 0:1:1:0, v/v), a C18 column (MeOH/$H_2O$, 9:1, v/v), and finally subjected to repeated reversed phase HPLC (MeOH/$H_2O$, 8:2, v/v) to yield hippuristanol (1, 23.0 mg), epihippuristanol (10, 15.1 mg), hippurin-1 (6, 6.7 mg), and epihippurin-1 (15, 1.5 mg). The $CH_2Cl_2$ extract was separated on a silica VFC column (hexane//EtOAc, 1:0, 10:1, 5:1, 2:1, 1:5, 0:1, v/v), followed by a Sephadex LH20 column ($CH_2Cl_2$/MeOH, 1:1, v/v). A fraction (400 mg) eluted with EtOAc was further separated on a silica gel column (/EtOAc) twice and finally subjected to reversed phase HPLC (MeOH/$H_2O$, 19-1, v/v) to give 2-desacetyl-hippurin-1 (8, 3.5 mg) and 2-desacetyl-epihippurin-1 (17, 20.4 mg). Additional amount of steroids 1, 6, 8, 10, 15, and 17 were obtained from other fractions.

Preparation of Steroids 7 and 16. A dried Indonesian specimen of the gorgonian *I. hippuris*. (3.2 kg) collected off Flores Island on August 2001 was extracted with acetone, and its EtOAc soluble portion (45.3 g) obtained. The extract was separated on a silica gel column twice followed by HPLC separation (silica, hexane/EtOAc, 1:5, v/v) to give 2-desacetyl-hippurin-1 3-acetate (7, 17.5 mg). Additional amounts of 7 were obtained by purification of other fractions. Compound 7 (24.6 mg) was treated with one drop of 1M hydrochloric solution in THF (1 mL) at RT for 3 hr. The mixture was partitioned between EtOAc and water, and the organic layer was dried over $Na_2SO_4$ and concentrated. The crude product was purified by HPLC (C18, MeOH/$H_2O$, 8:2, v/v) to give 22.1 mg of epimeric compound 16 (89%). Compound 16. colorless crystals, $^1$H NMR (CDCl$_3$) δ 5.12 (brs, 1H), 4.43 (m, 1H), 4.29 (brs, 1H), 3.89 (m, 1H), 2.24 (m, 1H), 2.12 (s, 3H), 1.34 (s, 3H), 1.28 (s, 6H), 1.06 (s, 3H), 0.98 (s, 3H), 0.94 (d, J=6.5 Hz, 3H), 0.83 (dd, J=11.0, 3.5 Hz, 1H).

Acetylation of hippuristanol (1) to give hippuristanol 3-acetate (2) and hippuristanol 3, 11-diacetate (3). A mixture of hippuristanol (1, 10.0 mg), acetic anhydride (0.2 mL), and dry pyridine (0.3 mL) was allowed to stand at room temperature for 13 days. The mixture was concentrated to remove excess acetic anhydride and pyridine. The crude product was separated by silica gel thin layer chromatography (TLC) (CHCl$_3$/EtOAc, 3:1, v/v) to give 8.5 mg of hippuristanol 3-acetate (2, 8.5 mg, 75%) and 1.7 mg of hippuristanol 3,11-diacetate (3, 14%). Hippuristanol 3,11-diacetate (3). glass, $[\alpha]_D^{22}$ +45.7° (c 0.44, CHCl$_3$); $^1$H NMR (CDCl$_3$) δ 5.32 (brq, J=2.8 Hz, 1H), 4.99 (brt, J=2.6 Hz, 1H), 4.30 (dt, J=7.0, 7.6 Hz, 1H), 3.11 (s, 1H), 2.37 (dd, J=13.4, 7.6 Hz, 1H), 2.28 (dd, J=14.4, 2.5 Hz, 1H), 2.04 (s, 3H), 2.02 (s, 3H), 1.29 (s, 3H), 1.26 (s, 3H), 1.23 (s, 3H), 1.20 (s, 3H), 0.98 (d, J=7.0 Hz, 3H), 0.88 (s, 3H); IR (KBr) 3500, 1720, 1235 cm$^{-1}$; EIMS m/z 546 (M$^+$, 0.4), 531 (3), 488 (19), 418 (13), 358 (84), 298 (100%).

Acetylation of epihippuristanol (10) to give epihippuristanol 3-acetate (11) and epihippuristanol 3,11-diacetate (12). Epihippuristanol (10, 10.0 mg) was acetylated in the same manner as described above for hippuristanol (1). The crude product was separated by silica gel TLC (CHCl$_3$/EtOAc, 3:1, v/v) to give 8.8 mg of epihippuristanol 3-acetate (11, 81%) and 1.7 mg of epihippuristanol 3,11-diacetate (12, 14%). Epihippuristanol 3,11-diacetate (12, hippurin-2). white solid, mp 253-256.5° C., $^1$H NMR (CDCl$_3$) δ 5.30 (m, 1H), 5.00 (brs, 1H), 4.44 (dt, J=5.5, 7.5 Hz, 1H), 2.25 (m, 2H), 2.04 (s, 3H), 2.01 (s, 3H), 1.29 (s, 3H), 1.27 (s, 3H), 1.22 (s, 3H), 0.98 (s, 3H), 0.94 (d, J=7.0 Hz, 3H), 0.89 (s, 3H); IR (KBr) 3520, 1725, 1250 cm$^{-1}$.

Oxidation of hippuristanol (1) to yield hippuristanol 11-one (4) and hippuristanol 3, 11-dione (5). To an ice-cooled solution of hippuristanol (1, 31.7 mg) in pyridine (0.5 mL), Cornforth reagent (0.7 mL) was added dropwise. The mixture was kept stirring for 30 min. in an ice bath, then 3 hr at RT. The mixture was taken up in ether and the suspension was filtered. The filtrate was washed with dilute hydrochloric acid, dried over $Na_2SO_4$, and concentrated. The resulting product was separated on silica TLC (CHCl$_3$/EtOAc, 3:1, v/v) to give 8.8 mg of hippuristanol 11-one (4, 28%) and 17.7 mg of hippuristanol 3,11-dione (5, 56%). Hippuristanol 3,11-dione (5). white crystals. mp 181-183.5° C.; $^1$H NMR (CDCl$_3$) δ 4.42 (m, 2H), 3.02 (s, 1H), 2.82 (ddd, J=13.0, 6.5, 2.0 Hz, 1H), 2.63 (d, J=12.0 Hz, 1H), 2.45 (dt, J=6.5, 14.5 Hz, 1H), 2.37 (dd, J=13.0, 8.0 Hz, 1H), 1.31 (s, 3H), 1.22 (s, 6H), 1.20 (s, 3H), 1.11 (s, 3H), 0.99 (d, J=7.0 Hz, 3H); $^{13}$C NMR (CDCl$_3$) δ 211.6, 210.0, 115.0, 84.9, 80.4, 79.1, 63.9, 63.4, 58.8, 54.5, 46.9, 46.3, 44.3, 41.8, 40.5, 38.0, 37.0, 35.5, 35.2, 33.7, 32.4, 28.7, 28.5, 28.2, 23.0, 17.3, 14.8, 11.0; IR (KBr) 3510, 1695 cm$^{-1}$; EIMS m/z 458 (M$^+$, 5), 316 (92), 84 (100%).

Oxidation of epihippuristanol (10) to give epihippuristanol 11-one (13) and epihippuristanol 3,11-dione (14). Epihippuristanol (10, 31.4 mg) was oxidized in the same fashion as described above for hippuristanol (1). The crude product was separated by TLC (CHCl$_3$/EtOAc, 1:1, v/v) to give 12.6 mg of epihippuristanol 11-one (13, 40%) and 14.0 mg of epihippuristanol 3,11-dione (14, 45%). Epihippuristanol 3,11-dione (14). white crystals, mp 226-229° C.; $^1$H NMR (CDCl$_3$) δ 4.48 (brq, J=7.0 Hz, 1H), 2.82 (ddd, J=13, 6.5, 2 Hz, 1H), 2.57 (d, J=12 Hz, 1H), 2.45 (dt, J=6.5, 14 Hz, 1H), 1.30 (s, 3H), 1.28 (s, 3H), 1.22 (s, 3H), 1.08 (s, 3H), 0.98 (s, 3H), 0.94 (d, J=7 Hz, 3H); $^{13}$C NMR (CDCl$_3$) δ 211.4, 209.9, 118.6, 84.5, 81.9, 79.0, 64.1, 63.2, 58.2, 55.8, 47.0, 45.9, 44.3, 41.0, 39.6, 38.0, 37.1, 35.8 (2C), 35.3, 32.3, 31.5, 29.0, 28.2, 26.0, 23.0, 17.6, 14.0, 11.1; IR (KBr) 3450, 1700 cm$^{-1}$; EIMS m/z 458 (M$^+$, 6), 443 (16), 400 (7), 330 (32), 315 (100%).

Preparation of 2-Desacetyl-hippurin-1 2-glutarate (9) and 2-Desacetyl-epihippurin-1 2-glutarate (18). A mixture of 2-desacetyl-hippruin-1 (8, 9.6 mg), glutaric anhydride (14 mg), and pyridine (0.1 mL) was allowed to stand at 70° C. for two days. After removal of pyridine, the crude product was separated by silica TLC (EtOAc), then by HPLC (C18, MeOH/H$_2$O, 9:1, v/v) to give 2.9 mg of glutarate (9, 24%). Compound 18 was prepared by treating compound 17 (23.6 mg) with glutaric anhydride and pyridine in the same way as described above for 2-desacetyl-hippruin-1 (8). The product was separated by silica TLC (EtOAc) followed by silica HPLC (hexane/EtOAc, 1:4, v/v) to give 3.4 mg of glutarate (18, 11%). amorphous solid, $^1$H NMR (CDCl$_3$) δ 5.00 (m, 1H), 4.43 (dt, J=7.5, 5.5 Hz, 1H), 4.26 (brs, 1H), 4.06 (brs, 1H), 2.42 (m, 2H), 2.25 (m, 2H), 2.14 (dd, J=14.5, 2.5 Hz, 1H), 1.33 (s, 3H), 1.30 (s, 3H), 1.27 (s, 3H), 1.10 (s, 3H), 0.98 (s, 3H), 0.94 (d, J=7.0 Hz, 3H).

Steroids 1, 6, 8, 10, 15, and 17steroids were identified by comparing their $^1$H and $^{13}$C NMR data with those previously isolated by Higa et al.

Hippuristanol 3-acetate (2). amorphous solid, $^1$H NMR (CDCl$_3$) δ 5.00 (brs, 1H), 4.29 (2H, m), 3.19 (s, 1H), 2.37 (dd, J=13.5, 7.5 Hz, 1H), 2.20 (dd, J=14.0, 2.5 Hz, 1H), 2.04 (s, 3H), 1.39 (s, 3H), 1.31 (s, 3H), 1.22 (s, 3H), 1.19 (s, 3H), 1.05 (s, 3H), 0.98 (d, J=7.0 Hz, 3H); IR (KBr) 3510, 1715, 1240 cm$^{-1}$; EIMS m/z 505 ([M+1]$^+$), 489 (2), 283 (100%).

Hippuristanol 11-one (4). white crystals. mp 205.5-208° C., $^1$H NMR (CDCl$_3$) δ 4.42 (brdt, J=7.0, 7.5 Hz, 1H), 4.03 (brs, 1H), 3.01 (s, 1H), 2.57 (d, J=11.9 Hz, 1H), 2.36 (dd, J=13.7, 8.0 Hz, 1H), 2.26 (dt, J=13.4, 3.0 Hz, 1H), 2.19 (d, J=11.9 Hz, 1H), 2.09 (m, 1H), 2.03 (d, J=8.8 Hz, 1H), 1.31 (s, 3H), 1.21 (s, 3H), 1.19 (s, 3H), 1.08 (s, 3H), 1.01 (s, 3H), 0.98 (d, J=7.0 Hz, 3H); $^{13}$C NMR (CDCl$_3$) δ 210.6, 115.0, 84.8, 80.5, 79.1, 66.3, 64.5, 63.4, 59.0, 54.9, 46.4, 41.8, 40.5, 38.9, 35.8, 35.6, 35.3, 33.6, 32.8, 30.9, 28.9, 28.7, 28.5, 27.9, 23.0, 17.2, 14.8, 10.8; IR (KBr) 3470, 1705 cm$^{-1}$; EIMS m/z 460 (M$^+$, 1), 402 (8), 317 (99), 129 (100%).

Glutarate 9. amorphous solid, $^1$H NMR (CDCl$_3$) δ 5.00 (ddd, J=11.8, 4.5, 3.0 Hz, 1H), 4.30 (brq, J=6.5 Hz, 1H), 4.25 (brs, 1H), 4.05 (brs, 1H), 3.21 (brs, 1H), 2.46 (m, 3H), 2.37 (dd, J=7.6, 13.4 Hz, 1 H), 2.17 (brd, J=14.0 Hz, 1H), 2.00 (m, 1H), 1.37 (s, 3H), 1.31 (s, 3H), 1.21 (s, 3H), 1.19 (s, 3H), 1.10 (s, 3H), 0.97 (d, J=7 Hz, 3H); $^{13}$C NMR (CDCl$_3$) δ 175.9, 172.1, 118.6, 84.2, 82.7, 79.0, 72.9, 68.0, 67.4, 66.3, 60.4, 58.2, 57.9, 48.8, 42.1, 41.0, 39.9, 39.0, 37.4, 36.7, 33.5, 32.7, 32.1, 31.6, 29.6, 29.1, 27.1, 26.9, 23.0, 20.0, 19.4,15.1,13.9.

Epihippuristanol 3-acetate (11). white solid, mp 193.5-195° C., $^1$H NMR (CDCl$_3$) δ 5.01 (brs, 1H), 4.44 (dt, J=5.0, 7.5 Hz, 1H), 4.30 (brs, 1H), 2.26 (m, 1H), 2.16 (dd, J=2.5, 14.0 Hz, 1H), 2.04 (s, 3H), 1.34 (s, 3H), 1.30 (s, 3H), 1.28 (s, 3H), 1.04 (s, 3H), 0.99 (s, 3H), 0.94 (d, J=7.0 Hz, 3H); IR (KBr) 3490, 1710, 1245 cm$^{-1}$; EIMS m/z 504 (M$^+$, 2), 489 (3), 446 (16), 376 (60), 358 (100%).

Epihippuristanol 3,11-diacetate (12, hippurin-2). white solid, mp 253-256.5° C., $^1$H NMR (CDCl$_3$) δ 5.30 (m, 1H), 5.00 (brs, 1H), 4.44 (dt, J=5.5, 7.5 Hz, 1H), 2.25 (m, 2H), 2.04 (s, 3H), 2.01 (s, 3H), 1.29 (s, 3H), 1.27 (s, 3H), 1.22 (s, 3H), 0.98 (s, 3H), 0.94 (d, J=7.0 Hz, 3H), 0.89 (s, 3H); IR (KBr) 3520, 1725, 1250 cm$^{-1}$.

Epihippuristanol 11-one (13). white crystals, mp 254-257° C.; $^1$H NMR (CDCl$_3$) δ 4.49 (q, J=7.1 Hz, 1H), 4.04 (brs, 1H), 2.51 (d, J=11.9 Hz, 1H), 2.25 (d, J=11.9 Hz, 1H), 1.29 (s, 3H), 1.28 (s, 3H), 1.05 (s, 3H), 1.01 (s, 3H), 0.98 (s, 3H), 0.94 (d, J=7.0 Hz, 3H); $^{13}$C NMR (CDCl$_3$) δ 210.5, 118.6, 84.4, 81.9, 79.1, 66.3, 64.6, 63.1, 58.4, 56.1, 45.9, 41.0, 39.6, 39.0, 35.8, 35.3, 32.7, 31.4, 30.9, 29.0, 28.9, 27.9, 25.8, 23.0, 17.6, 14.0, 10.9; IR (KBr) 3545, 3480, 1690 cm$^{-1}$; EIMS m/z 460 (M$^+$, 3), 445 (0.7), 402 (6), 332 (41), 317 (100%).

Compound 19. colorless crystals, mp: 240° C.; [α]$_D^{24}$– 38.0° (c 2.41, CHCl$_3$); $^1$H NMR (CDCl$_3$) δ 5.31 (s, 1H), 5.00 (brs 1 H), 4.53 (q, J=7 Hz, 1H), 4.24 (brs 1H), 2.69 (dd, J=14.5, 3.5 Hz, 1H), 2.61 (d, J=6.5 Hz, 1H), 2.28 (m, 1H), 2.12 (m, 1H), 2.06 (m, 1H), 2.04 (s, 3H), 1.87 (m, 1H), 1.82 (m, 2H), 1.74 (m, 1H), 1.71 (m, 2H), 1.64 (m, 1H), 1.61 (dd, J=14.5, 4 Hz, 1H), 1.48 (m, 3H), 1.41 (s, 3H), 1.41 (m, 1H), 1.34 (m, 1H), 1.29 (s, 3H), 1.27 (m, 1H), 1.18 (m, 2H), 1.00 (s, 3H), 096 (s, 3H), 0.93 (d, J=7 Hz, 3H), 0.79 (m, 1H); $^{13}$C NMR (CDCl$_3$) δ 170.6 s, 117.9 s, 101.3 d, 90.7 s, 84.7 s, 80.6 d, 70.0 d, 66.0 d, 64.3 d, 58.5 d, 56.1 s, 56.0 d, 41.1 d, 40.5 d, 39.2 t, 38.7 t, 35.9 s, 32.4 t, 33.7 t, 32.1 t, 32.1 t, 31.0 d, 29.0 q, 27.4 t, 25.6 t, 22.8 q, 21.4 q, 19.6 q, 14.4 q, 13.9 q; positive NOEs: H-6β/H-8, H-8/H-18, H-12β/H-21, H-12α/H-16, H-14/H-16, H-15β/H-18, H-16/H-17, H-17/H-21, and H-21/H-23α; IR (KBr) 3470, 3300, 1730, 1240 cm$^{-1}$; EIMS m/z 500 (M–H$_2$O), 485 (4), 442 (4), 372 (100%). The stereochemistry at C-18 was elucidated to be R configuration by positive NOEs between the proton pairs: H-18/H-8 and H-18/H-15β.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

REFERENCES

1. Adwankar, M. K., D. D. Khandalekar, and M. P. Chitnis. 1984. Combination chemotherapy of early and advanced murine P388 leukaemia with bouvardin, cis-diamminedichloroplatinum and vincristine. Oncology 41:370-3.
2. Ahuja, D., A. Geiger, J. M. Ramanjulu, M. D. Vera, B. SirDeshpande, A. Pfizenmayer, M. Abazeed, D. J. Krosky, D. Beidler, M. M. Joullie, and P. L. Toogood. 2000. Inhibition of protein synthesis by didemnins: cell potency and SAR. J Med Chem 43:4212-8.
3. Ahuja, D., M. D. Vera, B. V. SirDeshpande, H. Morimoto, P. G. Williams, M. M. Joullie, and P. L. Toogood. 2000. Inhibition of protein synthesis by didemnin B: how EF-1alpha mediates inhibition of translocation. Biochemistry 39:4339-46.
4. Andrus, L., P. Szabo, R. W. Grady, A. R. Hanauske, T. Huima-Byron, B. Slowinska, S. Zagulska, and H. M. Hanauske-Abel. 1998. Antiretroviral effects of deoxyhypusyl hydroxylase inhibitors: a hypusine-dependent host cell mechanism for replication of human immunodeficiency virus type 1 (HIV-1). Biochem Pharmacol 55:1807-18.
5. Antony, M., K. P. Gupta, K. K. Janardanan, and N. K. Mehrotra. 1991. Inhibition of mouse skin tumor promotion by tenuazonic acid. Cancer Lett 61:21-5.
6. Benz, J., H. Trachsel, and U. Baumann. 1999. Crystal structure of the ATPase domain of translation initiation factor 4A from *Saccharomyces cerevisiae*—the prototype of the DEAD box protein family. Structure Fold Des 7:671-9.

7. Bernstein, H. D., N. Sonenberg, and D. Baltimore. 1985. Poliovirus mutant that does not selectively inhibit host cell protein synthesis. Mol Cell Biol 5:2913-23.

8. Caruthers, J. M., E. R. Johnson, and D. B. McKay. 2000. Crystal structure of yeast initiation factor 4A, a DEAD-box RNA helicase. Proc Natl Acad Sci USA 97:13080-5.

9. Chan, C. C., J. Dostie, M. D. Diem, W. Feng, M. Mann, J. Rappsilber, and G. Dreyfuss. 2004. eIF4A3 is a novel component of the exon junction complex. Rna 10:200-9.

10. Chitnis, M., R. Menon, M. Adwankar, and K. Satyamoorthy. 1985. Inhibition of macromolecular synthesis in P388 mouse leukemia ascites cells by bouvardin (NSC 259968). Tumori 71:261-6.

11. Conroy, S. C., T. E. Dever, C. L. Owens, and W. C. Merrick. 1990. Characterization of the 46,000-dalton subunit of eIF-4F. Arch Biochem Biophys 282:363-71.

12. Dong, Z., L. H. Liu, B. Han, R. Pincheira, and J. T. Zhang. 2004. Role of eIF3 p170 in controlling synthesis of ribonucleotide reductase M2 and cell growth. Oncogene.

13. Ferraiuolo, M. A., C. S. Lee, L. W. Ler, J. L. Hsu, M. Costa-Mattioli, M. J. Luo, R. Reed, and N. Sonenberg. 2004. A nuclear translation-like factor eIF4AIII is recruited to the mRNA during splicing and functions in nonsense-mediated decay. Proc Natl Acad Sci U S A 101:4118-23.

14. Gonzalez, N., M. A. Barral, J. Rodriguez, and C. Jimenez. 2001. New cytotoxic steroids from the gorgonian *Isis hippuris*. Structure-activity studies. Tetrahedron 57:3487-3497.

15. Grifo, J. A., R. D. Abramson, C. A. Satler, and W. C. Merrick. 1984. RNA-stimulated ATPase activity of eukaryotic initiation factors. J Biol Chem 259:8648-54.

16. Grollman, A. P. 1967. Inhibitors of protein biosynthesis. II. Mode of action of anisomycin. J. Biol. Chem. 242:3226-3233.

17. Hanauske-Abel, H. M., M. H. Park, A. R. Hanauske, A. M. Popowicz, M. Lalande, and J. E. Folk. 1994. Inhibition of the G1-S transition of the cell cycle by inhibitors of deoxyhypusine hydroxylation. Biochim Biophys Acta 1221:115-24.

18. Hershey, J. W. B., and W. C. Merrick. 2000. Initiation of Protein Synthesis. Cold Spring Harbor Laboratory Press, Cold Spring Harbor.

19. Hershey, J. W. B., and S. Miyamoto. 2000. Translational Control and Cancer. Cold Spring Harbor Laboratory Press, Cold Spring Harbor.

20. Heys, S. D., K. G. Park, M. A. McNurlan, A. G. Calder, V. Buchan, K. Blessing, O. Eremin, and P. J. Garlick. 1991. Measurement of tumour protein synthesis in vivo in human colorectal and breast cancer and its variability in separate biopsies from the same tumour. Clin Sci (Lond) 80:587-93.

21. Higa, T., and J. Tanaka. 1981. 18-oxygenated polyfunctional steroids from the gorgonian *Isis hippuris*. Tetrahed. Lett. 22:2777-2780.

22. Higa, T., J. Tanaka, and K. Tachibana. 1981. 18-oxygenated polyfunctional steroids from the gorgonian *Isis hippuris*. Tetrahed. Lett. 22:2777-2780.

23. Higa, T., J. Tanaka, Y. Tsukitani, and H. Kikuchi. 1981. Hippuristanols, cytotoxic polyoxygenated steroids from the gorgonian *Isis hippuris*. Chem Lett. 11:1647-1650.

24. Hofs, H. P., D. J. Wagener, V. De Valk-Bakker, H. Van Rennes, A. J. Van Zeist, L. A. Van Den Broek, and H. C. Ottenheijm. 1992. Potentiation of cisplatin antitumour activity by Ethyldeshydroxy-Sparsomycin in L1210 leukemia. Anticancer Res 12:167-70.

25. Hofs, H. P., D. J. Wagener, D. De Vos, H. C. Ottenheijm, H. J. Winkens, P. H. Bovee, and W. J. De Grip. 1995. Antitumour activity and retinotoxicity of ethyldeshydroxy-sparsomycin in mice. Eur J Cancer 9:1526-30.

26. Johnson, E. R., and D. B. McKay. 1999. Crystallographic structure of the amino terminal domain of yeast initiation factor 4A, a representative DEAD-box RNA helicase. Rna 5:1526-34.

27. Kaczka, E. A., C. O. Gitterman, E. L. Dulaney, M. C. Smith, D. Hendlin, H. B. Woodruff, and K. Folkers. 1964. Discovery of inhibitory activity of tenuazonic acid for growth of human adenocarcinoma-1. Biochem Biophys Res Commun. 14:54-57.

28. Kantarjian, H. M., M. Talpaz, V. Santini, A. Murgo, B. Cheson, and S. M. O'Brien. 2001. Homoharringtonine: history, current research, and future direction. Cancer 92:1591-605.

29. Lorsch, J. R., and D. Herschlag. 1998. The DEAD box protein eIF4A. A cycle of nucleotide and RNA-dependent conformational changes. Biochemistry 37:2194-206.

30. Lorsch, J. R., and D. Herschlag. 1998. The DEAD box protein eIF4A. A minimal kinetic and thermodynamic framework reveals coupled binding of RNA and nucleotide. Biochemistry 37:2180-93.

31. Muller, H. J., and J. Boos. 1998. Use of L-asparaginase in childhood ALL. Crit Rev Oncol Hematol 28:97-113.

32. Neshat, M. S., I. K. Mellinghoff, C. Tran, B. Stiles, G. Thomas, R. Petersen, P. Frost, J. J. Gibbons, H. Wu, and C. L. Sawyers. 2001. Enhanced sensitivity of PTEN-deficient tumors to inhibition of FRAP/mTOR. Proc Natl Acad Sci USA 98:10314-9.

33. Novac, O., A. S. Guenier, and J. Pelletier. 2004. Inhibitors of protein synthesis identified by a high throughput multiplexed translation screen. Nucleic Acids Res 32:902-15.

34. Ottenheijm, H. C., and L. A. van den Broek. 1988. The development of sparsomycin as an anti-tumour drug. Anticancer Drug Des 2:333-7.

35. Palacios, I. M., D. Gatfield, D. St Johnston, and E. Izaurralde. 2004. An eIF4AIII-containing complex required for mRNA localization and nonsense-mediated mRNA decay. Nature 427:753-7.

36. Pause, A., G. J. Belsham, A. C. Gingras, O. Donze, T. A. Lin, J. C. Lawrence, Jr., and N. Sonenberg. 1994. Insulindependent stimulation of protein synthesis by phosphorylation of a regulator of 5'-cap function. Nature 371:762-7.

37. Pause, A., N. Methot, Y. Svitkin, W. C. Merrick, and N. Sonenberg. 1994. Dominant negative mutants of mammalian translation initiation factor eIF-4A define a critical role for eIF-4F in cap-dependent and cap-independent initiation of translation. Embo J 13:1205-15.

38. Pause, A., and N. Sonenberg. 1992. Mutational analysis of a DEAD box RNA helicase: the mammalian translation initiation factor eIF-4A. Embo J 11:2643-54.

39. Pisarev, A. V., L. S. Chard, Y. Kaku, H. L. Johns, I. N. Shatsky, and G. J. Belsham. 2004. Functional and structural similarities between the internal ribosome entry sites of hepatitis C virus and porcine teschovirus, a picornavirus. J Virol 78:4487-97.

40. Podsypanina, K., R. T. Lee, C. Politis, I. Hennessy, A. Crane, J. Puc, M. Neshat, H. Wang, L. Yang, J. Gibbons, P. Frost, V. Dreisbach, J. Blenis, Z. Gaciong, P. Fisher, C. Sawyers, L. Hedrick-Ellenson, and R. Parsons. 2001. An inhibitor of mTOR reduces neoplasia and normalizes p70/S6 kinase activity in Pten+/- mice. Proc Natl Acad Sci USA 98:10320-5.

41. Poulin, F., A. C. Gingras, H. Olsen, S. Chevalier, and N. Sonenberg. 1998. 4E-BP3, a new member of the eukaryotic initiation factor 4E-binding protein family. J Biol Chem 273:14002-7.
42. Rao, C. B., K. V. Ramana, D. V. Rao, E. Fahy, and J. D. Faulkner. 1988. Metabolites of the gorgonian *Isis hippuris* from India. J. Nat. Products. 51:954-958.
43. Ray, B. K., T. G. Lawson, J. C. Kramer, M. H. Cladaras, J. A. Grifo, R. D. Abramson, W. C. Merrick, and R. E. Thach. 1985. ATP-dependent unwinding of messenger RNA structure by eukaryotic initiation factors. J Biol Chem 260:7651-8.
44. Richter-Cook, N. J., T. E. Dever, J. O. Hensold, and W. C. Merrick. 1998. Purification and characterization of a new eukaryotic protein translation factor. Eukaryotic initiation factor 4H. J Biol Chem 273:7579-87.
45. Rogers, G. W., Jr., N. J. Richter, and W. C. Merrick. 1999. Biochemical and kinetic characterization of the RNA helicase activity of eukaryotic initiation factor 4A. J Biol Chem 274:12236-44.
46. Shen, Y.-C., C. V. S. Prakash, and Y.-T. Chang. 2001. Two new polyhydroxysteroids from the gorgonian *Isis hippuris*. Steroids 66:721-725.
47. Sheu, J.-H., S.-P. Chen, P.-J. Sung, M. Y. Chiang, and C.-F. Dai. 2000. Hippuristerone A, a novel polyoxygenated steroid from the gorgonian *Isis Hippuris*. Tetrahed. Lett. 41:7885-7888.
48. Shibuya, T., T. O. Tange, N. Sonenberg, and M. J. Moore. 2004. eIF4AIII binds spliced mRNA in the exon junction complex and is essential for nonsense-mediated decay. Nat Struct Mol Biol 11:346-51.
49. Sonenberg, N. 1981. ATP/Mg++-dependent cross-linking of cap binding proteins to the 5' end of eukaryotic mRNA. Nucleic Acids Res 9:1643-56.
50. Svitkin, Y. V., A. Pause, A. Haghighat, S. Pyronnet, G. Witherell, G. J. Belsham, and N. Sonenberg. 2001. The requirement for eukaryotic initiation factor 4A (eIF4A) in translation is in direct proportion to the degree of mRNA 5' secondary structure. Rna 7:382-94.
51. Tanaka, J., A. Trianto, M. Musman, H. H. Issa, I. I. Ohtani, T. Ichiba, T. Higa, W. Y. Yoshida, and P. J. Scheuer. 2002. New polyoxygenated steroids exhibiting reversal of multidrug resistance from the gorgonian *Isis hippuris*. Tetrahed. Lett. 58:6259-6266.
52. Tatsuo, H., J. Tanaka, T. Yasumasa, and K. Hiroyuki. 1981. Hippuristanols, cytotoxic polyoxygenated steroids from the gorgonian *Isis Hippuris*. Chem. Lett. 11:1647-1650.
53. Uchida, N., S. Hoshino, H. Imataka, N. Sonenberg, and T. Katada. 2002. A novel role of the mammalian GSPT/eRF3 associating with poly(A)-binding protein in Cap/Poly(A)-dependent translation. J Biol Chem 277:50286-92.
54. van den Broek, L. A., E. Lazaro, Z. Zylicz, P. J. Fennis, F. A. Missler, P. Lelieveld, M. Garzotto, D. J. Wagener, J. P. Ballesta, and H. C. Ottenheijm. 1989. Lipophilic analogues of sparsomycin as strong inhibitors of protein synthesis and tumor growth: a structure-activity relationship study. J Med Chem 32:2002-15.
55. Vera, M. D., and M. M. Joullie. 2002. Natural products as probes of cell biology: 20 years of didemnin research. Med Res Rev 22:102-45.
56. Wilson, J. E., T. V. Pestova, C. U. Hellen, and P. Sarnow. 2000. Initiation of protein synthesis from the A site of the ribosome. Cell 102:511-20.
57. Wilson, J. E., M. J. Powell, S. E. Hoover, and P. Sarnow. 2000. Naturally occurring dicistronic cricket paralysis virus RNA is regulated by two internal ribosome entry sites. Mol Cell Biol 20:4990-9.
58. Yoder-Hill, J., A. Pause, N. Sonenberg, and W. C. Merrick. 1993. The p46 subunit of eukaryotic initiation factor (eIF)-4F exchanges with eIF-4A. J Biol Chem 268:5566-73.
59. Zalacain, M., E. Zaera, D. Vazquez, and A. Jimenez. 1982. The mode of action of the antitumor drug bouvardin, an inhibitor of protein synthesis in eukaryotic cells. FEBS Lett 148:95-7.
60. Zalatnai, A., and J. Bocsi. 2003. Mimosine, a plant-derived amino acid induces apoptosis in human pancreatic cancer xenografts. Anticancer Res 23:4007-9.

The invention claimed is:

1. A method to treat a lymphoma in an individual in need thereof said method comprising:
administering to said individual a chemotherapeutic agent selected from the group consisting of doxorubicin, daunorubicin, cyclophosphamide, methotrexate, paclitaxel and alkylating agents, and a composition comprising an effective amount of a compound of formula I, or II, and a pharmaceutically acceptable carrier,

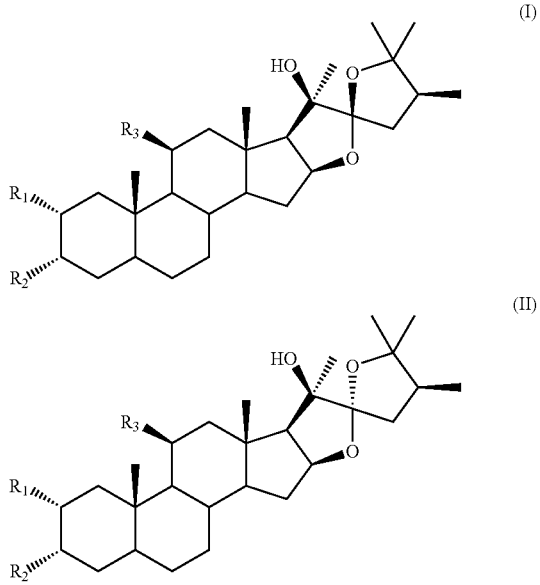

wherein
$R_1$, $R_2$ and $R_3$ are independently a hydrogen atom, a halogen atom, an oxygen atom of a ketone group, —$OR_4$, —C(O)H, —$CO_2$H, —C(O)$R_{18}$, —$NR_{11}R_{12}$, —SH, $C_1$-$C_{10}$ alkyl, $C_2$-$C_8$ alkenyl, $C_2$-$C_8$ alkynyl, $C_3$-$C_8$ cycloalkyl, $C_4$-$C_{10}$ cycloalkenyl, —(CH$_2$), $C_1$-$C_{10}$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aralkyl, —C(O)H, or a protected hydroxyl group,
$R_4$ and $R_{18}$ are a hydrogen atom alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aralkyl, —C(O)H, or a protecting group for a hydroxyl group;
$R_{11}$ and $R_{12}$ are independently hydrogen, $C_1$-$C_{10}$ alkyl, $C_6$-$C_{12}$ aralkyl.

2. The method as claimed in claim 1 wherein said compound is a compound of formula I or II and wherein
$R_1$=H, $R_2$=$R_3$=OH;
$R_1$=H, $R_2$=OC(O)CH$_3$, $R_3$=OH;
$R_1$=H, $R_2$=$R_3$=OC(O)CH$_3$;

$R_1$=H, $R_2$=OH, $R_3$=O;
$R_1$=H, $R_2$=$R_3$=O;
$R_1$=OC(O)CH$_3$, $R_2$=$R_3$=OH;
$R_1$=OH, $R_2$=OC(O)CH$_3$, $R_3$=OH;
$R_1$=$R_2$=$R_3$=OH; or
$R_1$=OCO(CH$_2$)$_3$COOH, $R_2$=$R_3$=OH.

3. The method as claimed in claim 1 wherein said compound is hippuristanol.

4. The method as claimed in claim 1 wherein said chemotherapeutic agent is selected from doxorubicin and cyclophosphamide.

5. The method as claimed in claim 1 wherein said chemotherapeutic agent is doxorubicin.

6. The method as claimed in claim 1 wherein said compound is hippuristanol and wherein said chemotherapeutic is doxorubicin or cyclophosphamide.

7. The method as claimed in claim 1 wherein said compound is hippurin-1.

8. The method as claimed in claim 1 wherein said compound is hippurin-1 and said chemotherapeutic is doxorubicin or cyclophosphamide.

9. The method as claimed in claim 1 wherein said compound is a compound of formula I.

10. The method as claimed in claim 9 wherein:
$R_1$=H, $R_2$=$R_3$=OH;
$R_1$=H, $R_2$=OC(O)CH$_3$, $R_3$=OH;
$R_1$=H, $R_2$=$R_3$=OC(O)CH$_3$;
$R_1$=H, $R_2$=OH, $R_3$=O;
$R_1$=H, $R_2$=$R_3$=O;
$R_1$=OC(O)CH$_3$, $R_2$=$R_3$=OH;
$R_1$=OH, $R_2$=OC(O)CH$_3$, $R_3$=OH;
$R_1$=$R_2$=$R_3$=OH(22R); or
$R_1$=OCO(CH$_2$)$_3$COOH, $R_2$=$R_3$=OH.

11. The method as claimed in claim 10 wherein said chemotherapeutic agent is doxorubicin or cyclophosphamide.

12. A method to treat lymphoma in an individual in need thereof, said method comprising administering a chemotherapeutic agent selected from doxorubicin and cyclophosphamide and a composition comprising an effective amount of a compound of formula I or II, and a pharmaceutically acceptable carrier,

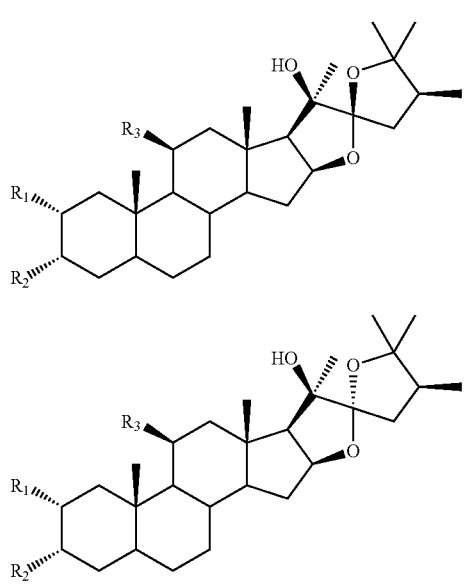

wherein
$R_1$, $R_2$ and $R_3$ are independently a hydrogen atom, a halogen atom, an oxygen atom of a ketone group, —OR$_4$, —C(O)H, —CO$_2$H, —C(O)R$_{18}$, —NR$_{11}$R$_{12}$, —SH, C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl, —(CH$_2$), C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl, C$_6$-C$_{12}$ aralkyl, —C(O)H, or a protected hydroxyl group, $R_4$ and $R_{18}$ are a hydrogen atom alkyl, C$_2$-C$_8$ alkenyl, C$_2$-C$_8$ alkynyl, C$_3$-C$_8$ cycloalkyl, C$_4$-C$_{10}$ cycloalkenyl, C$_6$-C$_{12}$ aralkyl, —C(O)H, or a protecting group for a hydroxyl group;

$R_{11}$ and $R_{12}$ are independently hydrogen, C$_1$-C$_{10}$ alkyl, C$_6$-C$_{12}$ aralkyl.

13. The method as claimed in claim 12 wherein said compound is a compound of formula I.

14. The method as claimed in claim 13 wherein said compound is a compound of formula I wherein,
$R_1$=H, $R_2$=$R_3$=OH;
$R_1$=H, $R_2$=OC(O)CH$_3$, $R_3$=OH;
$R_1$=H, $R_2$=$R_3$=OC(O)CH$_3$;
$R_1$=H, $R_2$=OH, $R_3$=O;
$R_1$=H, $R_2$=$R_3$=O;
$R_1$=OC(O)CH$_3$, $R_2$=$R_3$=OH;
$R_1$=OH, $R_2$=OC(O)CH$_3$, $R_3$=OH;
$R_1$=$R_2$=$R_3$=OH(22R); or
$R_1$=OCO(CH$_2$)$_3$COOH, $R_2$=$R_3$=OH.

15. A method to treat lymphoma in an individual in need thereof, said method comprising administering doxorubicin and a composition comprising an effective amount of a compound of formula I or II, and a pharmaceutically acceptable carrier,

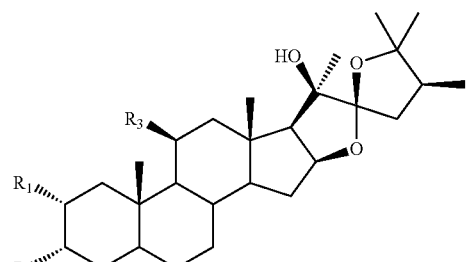
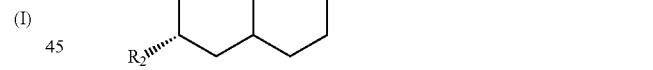
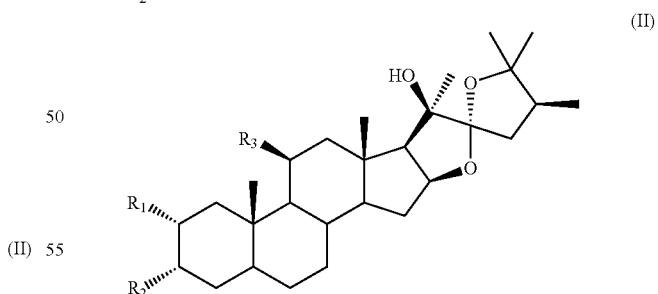

wherein
$R_1$, $R_2$ and $R_3$ are independently a hydrogen atom, a halogen atom, an oxygen atom of a ketone group, —OR$_4$, —C(O)H, —CO$_2$H, —C(O)R$_{18}$, —NR$_{11}$R$_{12}$, —SH, C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl, —(CH$_2$), C$_1$-C$_{10}$ alkyl, C$_2$-C$_8$ alkenyl, C$_2$-C$_8$ alkynyl, C$_3$-C$_8$ cycloalkyl, C$_4$-C$_{10}$ cycloalkenyl, C$_6$-C$_{12}$ aralkyl, —C(O)H, or a protected hydroxyl group, $R_4$ and $R_{18}$ are a hydrogen atom alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aralkyl, —C(O)H, or a protecting group for a hydroxyl group;

$R_{11}$ and $R_{12}$ are independently hydrogen, $C_1$-$C_{10}$ alkyl, $C_6$-$C_{12}$ aralkyl.

16. A method to treat lymphoma in an individual in need thereof, said method comprising administering doxorubicin and a composition comprising an effective amount of hippuristanol.

* * * * *